(12) United States Patent
Dinges

(10) Patent No.: US 11,782,054 B2
(45) Date of Patent: Oct. 10, 2023

(54) ANTIBODY-LINKED IMMUNO-SEDIMENTATION AGENT AND METHOD OF ISOLATING A TARGET FORM A SAMPLE USING SAME

(71) Applicant: CytoSed, Inc., Seattle, WA (US)

(72) Inventor: Warren L. Dinges, Seattle, WA (US)

(73) Assignee: CytoSed, Inc., Seattle, WA (US)

( * ) Notice: Subject to any disclaimer, the term of this patent is extended or adjusted under 35 U.S.C. 154(b) by 552 days.

(21) Appl. No.: 16/052,454

(22) Filed: Aug. 1, 2018

(65) Prior Publication Data

US 2019/0204307 A1 Jul. 4, 2019

Related U.S. Application Data

(63) Continuation of application No. 13/800,495, filed on Mar. 13, 2013, now abandoned, which is a continuation of application No. PCT/US2011/065157, filed on Dec. 15, 2011.

(60) Provisional application No. 61/423,391, filed on Dec. 15, 2010.

(51) Int. Cl.
| | |
|---|---|
| *G01N 33/53* | (2006.01) |
| *G01N 33/539* | (2006.01) |
| *G01N 33/537* | (2006.01) |
| *G01N 33/569* | (2006.01) |
| *C07K 16/00* | (2006.01) |

(52) U.S. Cl.
CPC ........... *G01N 33/539* (2013.01); *C07K 16/00* (2013.01); *G01N 33/5375* (2013.01); *G01N 33/56966* (2013.01); *G01N 33/56972* (2013.01); *G01N 33/56988* (2013.01); *G01N 2333/7051* (2013.01)

(58) Field of Classification Search
CPC ...... G01N 15/05; G01N 1/40; G01N 15/0272; G01N 2015/0288; G01N 2015/0294; G01N 33/96; G01N 2015/0073; G01N 33/491; G01N 2496/05; G01N 15/042; G01N 2001/4016; G01N 33/92; G01N 2333/4724; G01N 2400/22; G01N 2500/10; G01N 33/56972; G01N 2333/7051; G01N 2333/70514; G01N 33/5094; G01N 33/54313; A61M 1/3679; A61M 1/36; A61M 1/0209; A61M 2202/0439; A61M 1/34; A61M 2202/0441; B01D 67/009; B01D 69/144; B01D 71/28; B01D 71/38; B01D 71/44; B01D 71/52; B01D 71/72; B01D 15/327; B01D 21/26; B01D 69/12; B01L 2400/0409; B01L 2300/0874; B01L 2300/0825; B01L 3/50273; A61K 38/00; A61K 2039/505; A61K 35/16; A61K 35/12; A61K 2123/00; A61K 35/18; C12N 2502/14; C12N 2502/28; C12N 2533/40

See application file for complete search history.

(56) References Cited

U.S. PATENT DOCUMENTS

| | | | |
|---|---|---|---|
| 5,840,502 | A | 11/1998 | Van Vlasselaer |
| 5,877,299 | A | 3/1999 | Thomas et al. |
| 6,117,985 | A | 9/2000 | Thomas et al. |
| 6,448,075 | B1 | 9/2002 | Thomas et al. |
| 6,482,926 | B1 | 11/2002 | Thomas et al. |
| D490,531 | S | 5/2004 | Feldman |
| 6,750,326 | B2 | 6/2004 | Thomas et al. |
| 6,872,567 | B2 | 3/2005 | Thomas et al. |
| 6,979,534 | B1 | 12/2005 | Siegel |
| 7,135,335 | B2 | 11/2006 | Thomas et al. |
| 7,135,340 | B2 | 11/2006 | Wognum et al. |
| 7,205,157 | B2 | 4/2007 | Jurgensen et al. |
| 2004/0142463 | A1 | 6/2004 | Walker et al. |
| 2010/0136585 | A1 | 6/2010 | Schwind et al. |
| 2011/0003380 | A1 | 1/2011 | Miltenyi et al. |
| 2011/0004952 | A1 | 1/2011 | Bosio |
| 2011/0009837 | A1 | 1/2011 | Schreiner |
| 2011/0097313 | A1 | 4/2011 | Schonbrunn et al. |
| 2011/0111982 | A1 | 5/2011 | Woodside et al. |
| 2011/0233148 | A1 | 9/2011 | Antonchuk et al. |
| 2011/0269152 | A1 | 11/2011 | Miltenyi et al. |
| 2013/0266930 | A1 | 10/2013 | Dinges |

FOREIGN PATENT DOCUMENTS

| | | |
|---|---|---|
| EP | 0696933 | 4/1994 |
| JP | 2004-526452 A | 9/2004 |
| WO | WO 2000/073794 A2 | 12/2000 |
| WO | WO 2002/083262 A1 | 10/2002 |
| WO | WO 2006/094810 A2 | 9/2006 |

(Continued)

OTHER PUBLICATIONS

Adorno et al., "Red blood cell depletion of cord blood using hydroxyethylstarch double sedimentation: analysis of 40 cases," Clin. Lab. Haem. 20:341-343, 1998.

(Continued)

*Primary Examiner* — Carmencita M Belei
(74) *Attorney, Agent, or Firm* — COOLEY LLP

(57) ABSTRACT

The present disclosure is directed to antibody-linked immuno-sedimentation agent, the antibody being linked to a sedimentation agent by a non-antigen binding region of the antibody, and a method of isolating a target from a sample using the antibody-linked immuno-sedimentation agent. The methods involve forming a mixture including a sample with an antibody linked immuno-sedimentation agent and red blood cells under conditions sufficient to form red blood cell rouleaux and allow antibody-antigen binding.

8 Claims, 13 Drawing Sheets

(56) References Cited

FOREIGN PATENT DOCUMENTS

| WO | WO 2011/138609 A1 | 11/2011 |
| WO | WO 2012/083020 A2 | 6/2012 |

OTHER PUBLICATIONS

Dieterich et al., "Effect of intravenous hydroxyethyl starch on the accuracy of measuring hemoglobin concentration," Journal of Clinical Anesthesia 17:249-254, 2005.

Evans, D.I., "A dextran slide test for blood grouping," J Clin Pathol 24:285, 1971.

GE Healthcare, "Density Marker Beads (Product Information Sheet)", www.gelifesciences.com, Mar. 2006 [retrieved Nov. 4, 2007] (4 pages).

GE Healthcare, "Ficoll-Paque Premium (Product Information Sheet)", www.gelifesciences.com, 2005 [retrieved Nov. 4, 2007] (11 pages).

GE Healthcare, "Percoll Plus/Percoll (Product Information Sheet)", www.gelifesciences.com, Aug. 2006 [retrieved on Nov. 4, 2007] (8 pages).

International Search Report and Written Opinion for PCT/US2011/065157, dated Oct. 29, 2012 (17 pages).

International Preliminary Report on Patentability for PCT/US2011/065157, dated Jun. 27, 2013 (11 pages).

Invitrogen Corp., "Start your T cell research right: Dynabeads tube-based cell isolation (Product Information Sheet)", www.invitrogen.com, 2008 [retrieved on May 2, 2010] (6 pages).

Lee et al., "A Controlled Comparison of the Efficacy of Hetastarch and Pentastarch in Granulocyte Collections by Centrifugal Leukapheresis," Blood 86(12):4662-4666, 1995.

Maeda et al., "Inhibition and acceleration of erythrocyte aggregation induced by small macromolecules," Biochim. Biophys. Acta 843:128-136, 1985.

Miltenyi Biotec GmbH, "MACS Cell Separation Strategies (Product Information Sheet)", www.miltenyibiotec.com, 2008 [retrieved May 2, 2010] (2 pages).

Miltenyi Biotec GmbH, "MACS Technology: Gold standard in cell separation (Product Information Sheet)", www.miltenyibiotec.com, 2008 [retrieved May 2, 2010] (8 pages).

Mishler et al., "Increased Efficiency of Leukocyte Collection by the Addition of Hydroxyethyl Starch to the Continuous Flow Centrifuge," Blood 44(4), 1974.

Munoz et al., "Sedimentation method for preparation of postoperatively salvaged uwashed shed blood in orthopaedic surgery," British Journal of Anaesthesia 105(4):457-65, 2010.

Munoz et al., "Sedimentation method for preparation of postoperatively salvaged uwashed shed blood in orthopaedic surgery," Supplementary Data, British Journal of Anaesthesia 105(4):1-4, 2010.

Murphy et al., "An evaluation of cell separation techniques in a model mixed cell population," Journal of Cell Science, 102:789-798, 1992.

Neu et al., "Depletion-Mediated Red Blood Cell Aggregation in Polymer Solutions," Biophysical Journal, 83:2482-2490, 2002.

Perutelli et al., "Processing of Human Cord Blood by Three Different Procedures for Red Blood Cell Depletion and Mononuclear Cell Recovery," Vox Sanguinis 76:237-240, 1999.

Rock et al., "An in vitro method for predicting the efficacy of WBC separation using different starch preparations and anticoagulant ratios," Transfusion 40:1442-1445, Dec. 2000.

Schwinger et al., "Comparison of different methods for separation and ex vivo expansion of cord blood progenitor cells," Ann Hematol 78:364-370, 1999.

StemCell Technologies, Inc., "Ammonium Chloride Solution—RBC Lysis Buffer (Product Information Sheet)", www.stemcell.com, Oct. 2006 [retrieved on Nov. 27, 2007] (1 page).

StemCell Technologies, Inc., "EasySep Negative Selection Custom Cocktail for Human Cells: Human CD4 Enrichment from Whole Blood Treated with HetaSep (Product Information Sheet)", www.stemcell.com, Mar. 2007 [retrieved on Jun. 14, 2009] (3 pages).

StemCell Technologies, Inc., "Magnetic Cell Separation (Product Information Sheet)", www.stemcell.com, undated [retrieved on Nov. 4, 2007] (8 pages).

StemCell Technologies, Inc., "SpinSep (Product Information Sheet)", www.stemcell.com, undated [retrieved on Nov. 4, 2007] (4 pages).

StemCell Technologies, Inc., "What is RosetteSep? (Product Information Sheet)", www.stemcell.com, undated [retrieved on Nov. 4, 2007] (2 pages).

StemCell Technoloiges, Inc., "StemSep (Product Information Sheet)", www.stemcell.com, undated [retrieved on Jun. 14, 2009] (6 pages).

Tsang et al., "Dextran sedimentation in a semi-closed system for the clinical banking of umbilical cord blood," Transfusion, vol. 41, Mar. 2001.

Van Vlasselaer, "Density Adjusted Cell Sorting (DACS), A Novel Method to Remove Tumor Cells from Peripheral Blood and Bone Marrow Stem Cell Transplants," Paper, Department of Applied Immunology and Hematology, Activated Cell Therapy, Inc. [1995] 3rd International Symposium on Recent Advances in Hematopoietic Stem Cell Transplantation—Clinical Progress, New Technologies and Gene Therapy, San Diego, CA (2 pages).

PRIOR ART

ANTIBODY-LINKED IMMUNO-SEDIMENTATION AGENT AND METHOD OF ISOLATING A TARGET FORM A SAMPLE USING SAME

CROSS REFERENCE TO RELATED APPLICATIONS

This application is a continuation of U.S. Application Ser. No. 13/800,495, filed Mar. 13, 2013, which is a continuation of International PCT Patent Application No. PCT/US2011/065157, filed Dec. 15, 2011, now expired, which claims the benefit under 35 U.S.C. § 119(e) of U.S. Provisional Patent Application No. 61/423,391 filed Dec. 15, 2010. These applications are incorporated herein by reference in their entireties.

BACKGROUND OF THE DISCLOSURE

Field of the Disclosure

The present disclosure generally relates to the isolation of a target (e.g., cells and molecules) from a solution containing the target. More particularly, the present disclosure relates to a novel method of separating a target from a solution using an antibody-linked immuno-sedimentation agent (ALISA). Additionally, the present disclosure relates to the antibody-linked immuno-sedimentation agent itself.

Description of the Related Art

Many methods exist for the isolation of a target (e.g., cells, molecules, etc.) from a solution. Targets such as, for example, nucleic acids (e.g., DNA and RNA), proteins, and other molecules may be isolated by extraction, precipitation, chromatography, and immunoaffinity, among others. Techniques such as immunoadsorption use anti-target antibodies linked to a substrate such as, beads and magnetic particles. The target bound to the bead is then isolated from a sample by collecting the beads and removing the unbound components.

Many methods also exist for the isolation, enrichment, and purification of a target such as, for example, cells. Cell separation is a complex and well established art for sorting wanted cells from unwanted cells using a diverse set of techniques. One of the oldest cell separation methods is standard blood sedimentation. Blood that is allowed to stand under the force of gravity naturally sediments into a red blood cell (RBC) layer, a buffy coat layer with white blood cells (WBCs), and a plasma layer. The rate of this sedimentation, called the erythrocyte sedimentation rate (ESR), may be used as a laboratory marker of inflammation. The rate of sedimentation may be increased by the addition of a sedimentation agent and/or centrifugation. Erythrocyte sedimentation is a non-specific process that separates blood components crudely according to their densities. The method is dependent on the reversible process of RBC adhesion into rouleaux and rouleaux networks, and includes no antibody mediated separation of targets of interest. (See e.g., Maeda and Shiga, Biochim. Biophys. Acta 843: 128-136 (1985)).

Leukapheresis is a more complex method of cell sedimentation. In this method, blood is collected from a patient, sedimented on a continuous process with the WBCs (buffy coat) being removed, while the plasma and RBCs are returned to the patient.

Centrifugation may be combined with a density gradient to separate a target from unwanted components. Density gradients are formed using a media of specified density such as, for example, FICOLL-HYPAQUE and Percoll-sucrose. Components of the sample separate based on their migration through the density gradient during centrifugation. For example, a standard FICOLL-HYPAQUE at a density of 1.077 g/ml separates peripheral blood mononuclear cells (PBMCs), including lymphocytes and monocytes, from the higher density RBCs and neutrophils. As with a standard RBC sedimentation, there is no antibody mediated target separation.

Flow cytometry is another method used for cell separation. In flow cytometry, cells are suspended in a separation liquid and labeled with fluorophores directed to cell surface markers. Fluorophores may also be directed to intracellular targets. Antibodies such as, for example, anti-Cluster Determinant (anti-CD) antibodies (for example, anti-CD4, anti-CD8 or anti-CD56) may be conjugated to fluorophores to affect separations. The labeled and unlabeled cells are run through a flow cell where they are examined for their fluorescence, size, and granularity. In practice, multiple distinct fluorophores may be excited by different lasers and observed through different channels at once. The cells can then be directed to separate collection tubes based on their particular fluorescence, size, or granularity. Flow cytometry is an effective method for cellular analysis and cell separation, but is complex and equipment-intensive.

Another cell separation method employs affinity column chromatography. Affinity column chromatography involves a solid-phase such as, for example, polystyrene or agarose. The solid phase may be coupled with an affinity agent such as, for example, streptavidin. Biotinylated anti-CD antibodies can then be attached to the column. As a cell suspension flows through the column, the antibodies attached to the affinity support bind cells having the surface antigen of the anti-CD antibody. Other affinity agents suitable for use in such a process include, for example, glutathione-S-transferase (GST) that interacts with glutathione and histidine that pairs with nickel or cobalt. These affinity agents are not frequently used for cell separation techniques, however.

Another cell separation method uses magnetic beads. Magnetic beads may be directly or indirectly coupled to an antibody directed to a target. Targets interacting with the antibody-coupled magnetic bead may be separated from the suspension by applying a magnetic field. Unwanted components are then removed by a series of washing steps while the target is retained by the interaction with the magnetic beads and application of the magnetic field.

U.S. Pat. No. 6,117,985 discloses a separation method that uses antibodies to cell surface markers to form tetrameric antibody complexes (TAC). TACs are composed of an anti-target cell antibody, an anti-dextrin antibody, and two bridging antibodies that link the anti-target cell antibody with the anti-dextrin antibody. The TACs bind target cells to dextrin coated magnetic beads. Targets interacting with the TAC-coupled magnetic beads may be separated from the suspension by applying a magnetic field. Unwanted components are then removed by a series of washing steps while the target is retained by the TAC-mediated interaction with the magnetic beads and application of the magnetic field.

U.S. Pat. No. 7,135,335 discloses a separation method that uses antibodies to cell surface markers to form tetrameric antibody complexes (TAC), but without magnetic particles. In this case, TACs are composed of an anti-target cell antibody, an anti-erythrocyte antibody, and two bridging antibodies that link the anti-target cell antibody with the anti-erythrocyte antibody under conditions sufficient to form immunorosettes of the target cell and the erythrocytes.

During centrifugation, the target cells aggregate into the RBC layer via TAC-mediated immunorosettes. Other cells remain in the buffy coat layer. An aggregating agent may be used in the immunorosetting method; however, the aggregating agent is not linked to an antibody.

While many of these methods of cell separation are highly effective, they can be expensive, require multiple complex steps, and/or can be equipment-intensive. Accordingly, there exists a need for alternative reagents and methods for separating a target from a sample that are more cost and/or time effective. The present invention fulfills these needs and provides further related advantages.

SUMMARY OF THE DISCLOSURE

The present disclosure is generally directed to an antibody-linked immuno-sedimentation agent (ALISA) and to a method of isolating a target using the antibody-linked immuno-sedimentation agent. More specifically, in one aspect, the present disclosure is directed to an antibody-linked immuno-sedimentation agent that comprises at least one sedimentation agent and at least one antibody linked to the sedimentation agent, wherein the at least one antibody is linked to the sedimentation agent by a non-antigen binding region.

In another aspect, the present disclosure is directed to a method of obtaining a target from a sample. The method comprises forming a mixture comprising a sample, an antibody-linked immuno-sedimentation agent, and red blood cells, wherein the antibody-linked immuno-sedimentation agent comprises at least one sedimentation agent and at least one antibody linked to the at least one sedimentation agent, and further wherein the antibody is linked to the at least one sedimentation agent by a non-antigen binding region of the antibody. Once formed, the mixture is incubated under conditions sufficient to form a rouleaux, and then the target is recovered from the mixture. In various aspects, the rouleaux is formed by adsorption of the at least one sedimentation agent onto the red blood cells of the rouleaux. In one particular embodiment, once the rouleaux formation occurs, the rouleaux-containing mixture is allowed to phase separate in order to collect the target.

In another aspect, the present disclosure is directed to an antibody-linked immuno-sedimentation agent comprising at least one sedimentation agent selected from the group consisting of polyethylene glycol, dextran, and hydroxyethyl starch and at least one antibody linked to the at least one sedimentation agent, wherein the at least one antibody is linked to the at least one sedimentation agent by a non-antigen binding region and wherein the at least one antibody is selected from the group consisting of an anti-CD3 antibody, an anti-CD19 antibody, an anti-insulin antibody, an anti-CD34 antibody, an anti-CD4 antibody, an anti-CD14 antibody, an anti-CD16 antibody, an anti-CD19 antibody, an anti-CD20 antibody, an anti-CD36 antibody, an anti-CD56 antibody, an anti-CD123 antibody, an anti-TCRγ/δ antibody, an anti-glycophorin A antibody, and an anti-GP120 antibody.

In another aspect, the present disclosure is directed to a method of isolating a target from a sample. The method comprises forming a mixture comprising a sample, an antibody-linked immuno-sedimentation agent and red blood cells, wherein the antibody-linked immuno-sedimentation agent comprises at least one sedimentation agent selected from the group consisting of polyethylene glycol, dextran, and hydroxyethyl starch; and at least one antibody linked to the at least one sedimentation agent by a non-antigen binding region of the antibody, wherein the antibody is selected from the group consisting of an anti-CD3 antibody, an anti-CD19 antibody, an anti-insulin antibody, an anti-CD34 antibody, an anti-CD4 antibody, an anti-CD14 antibody, an anti-CD16 antibody, an anti-CD19 antibody, an anti-CD20 antibody, an anti-CD36 antibody, an anti-CD56 antibody, an anti-CD123 antibody, an anti-TCRγ/δ antibody, an anti-glycophorin A antibody, and an anti-GP120 antibody; incubating the mixture under conditions sufficient to form a rouleaux and allow the antibody to bind to an antigen present in the mixture; and recovering a target from the mixture.

BRIEF DESCRIPTION OF THE DRAWINGS

The disclosure will be better understood, and features, aspects and advantages other than those set forth above will become apparent, when consideration is given to the following detailed description thereof. Such detailed description makes reference to the following drawings, wherein.

Figure 1:
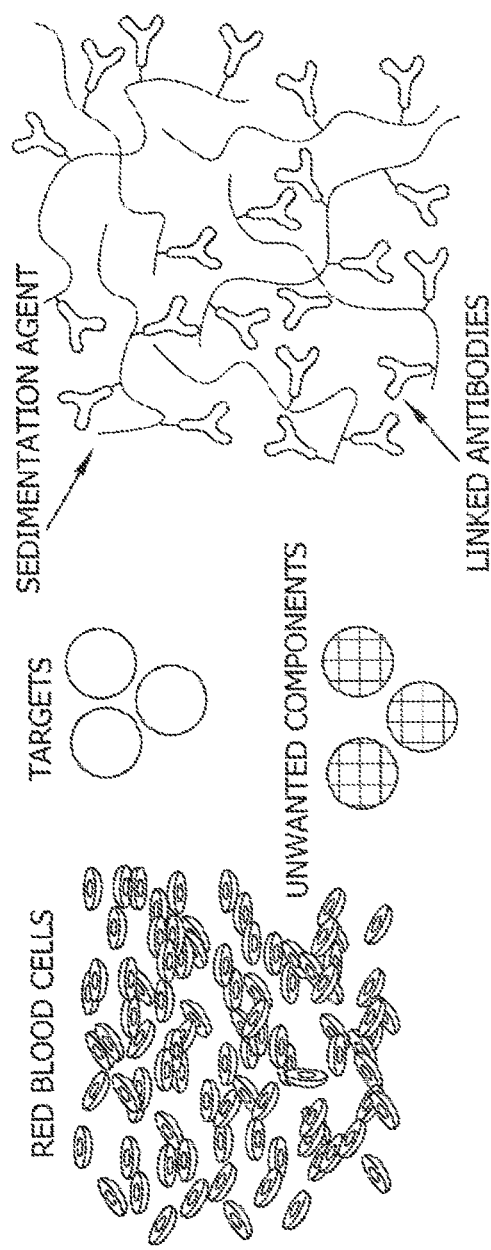
FIG. 1 is an illustration showing at least four components including an erythrocyte (RBC) matrix, targets (open circles), unwanted components (hatched circles), and ALISA comprising a sedimentation agent with linked antibodies used in the methods of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, suitable methods and materials are described below.

In accordance with the present disclosure, an antibody-linked immuno-sedimentation agent (ALISA) has been discovered that advantageously allows for or enables the separation of a target (molecule, cell, etc.) from a sample in a more efficient and/or cost-effective manner, at least in part by inducing the formation by RBCs (present in a mixture containing the target and the ALISA) into rouleaux and/or rouleaux networks. Specifically, the ALISA comprises at least one sedimentation agent and at least one antibody linked to the sedimentation agent, wherein the antibody is linked to the sedimentation agent by a non-antigen binding region. Accordingly, methods for isolating a target from a sample have also been discovered that use the ALISA. The antibody of the ALISA binds to an antigen of a target or a non-target, resulting in the co-sedimentation of the target or non-target with the rouleaux and/or rouleaux networks.

In addition to being used with any sample that contains red blood cells, the method of the present disclosure is useful for the isolation of targets from samples lacking or deficient in red blood cells. Thus, the methods of the present disclosure may be used as an alternative method for isolating targets by methods such as, for example, precipitation, affinity chromatography, magnetic particles, and flow cytometry, among others. Compared to other prior art methods that use red blood cells to form rosettes and/or immunorosettes, the methods of the present disclosure do not require combinations of separate antibodies that bind red blood cells and targets. The methods of the present disclosure further do not require linking the antibodies directed to the target with the antibodies directed to the red blood cells to allow the formation of rosettes. Thus, the methods of the present disclosure eliminate reagents, required steps, and expensive equipment that are necessary in other prior art methods.

Antibody-Linked Immuno-Sedimentation Agents (ALISA)

One aspect of the present disclosure is directed to an antibody-linked immuno-sedimentation agent (ALISA). ALISA comprise at least one sedimentation agent and at least one antibody linked to the at least one sedimentation agent, wherein the antibody linked to the sedimentation agent is linked by a non-antigen binding region of the antibody as further detailed herein below. Alternatively, ALISA may consist of or consist essentially of at least one sedimentation agent and at least one antibody linked to the at least one sedimentation agent, wherein the antibody linked to the sedimentation agent is linked by a non-antigen binding region of the antibody as further detailed herein below.

Advantageously, the ALISA includes an antibody directed at or is designed for binding a target or unwanted component without using a second antibody directed at erythrocytes (RBCs) such as, for example, anti-glycophrin A, that is used in methods required to form rosettes. The immunological co-targeting of antibodies of interest linked to a second antibody against RBC cell surface markers is an unnecessary complication and expense. ALISA advantageously eliminates the need to use an anti-RBC antibody, and separates a target or unwanted component by coupling an antibody against an anti-target or anti-unwanted component directly to a sedimentation agent to form RBC stacks (called rouleaux) and rouleaux networks during immuno-sedimentation.

In certain aspects, the present disclosure is directed to an antibody-linked immuno-sedimentation agent comprising at least one sedimentation agent selected from the group consisting of polyethylene glycol, dextran, and hydroxyethyl starch and at least one antibody linked to the at least one sedimentation agent, wherein the at least one antibody is linked to the at least one sedimentation agent by a non-antigen binding region and wherein the at least one antibody is selected from the group consisting of an anti-CD3 antibody, an anti-CD19 antibody, an anti-insulin antibody, an anti-CD34 antibody, an anti-CD4 antibody, an anti-CD14 antibody, an anti-CD16 antibody, an anti-CD19 antibody, an anti-CD20 antibody, an anti-CD36 antibody, an anti-CD56 antibody, an anti-CD123 antibody, an anti-TCRγ/δ antibody, an anti-glycophorin A antibody, and an anti-GP120 antibody.

Sedimentation Agents

The antibody-linked sedimentation agent used in the method of the present disclosure includes at least one sedimentation agent and at least one (or one type of) antibody linked or attached thereto. In other aspects, the ALISA includes more than one sedimentation agent. The selection of the sedimentation agent(s) is dependent on a variety of variables that one skilled in the art can optimize. Variables such as, for example, concentration of the sedimentation agent, targets, and RBCs, molecular weight of the sedimentation agent, temperature, the ratio of targets to antibodies, the ratio of sedimentation agent to RBCs, the rate/time of sedimentation desired, the desired rate/time of rouleaux formation, and/or the desired rate/time of rouleaux network formation, among others, may be considered by one skilled in the art when selecting the sedimentation agent.

The sedimentation agent that is suitable for use in preparing the ALISA of the present disclosure may be an enormously diverse group of agents. Properties or reagents guiding selection of a suitable sedimentation agent include the ability of inducing RBC rouleaux formation and linking, either directly or indirectly, the desired antibodies (i.e., antibodies that will in turn bind the desired target or unwanted component). The sedimentation agent may be a soluble, a semi-soluble, or an insoluble macromolecule. It may be advantageous to use a semi-soluble or insoluble sedimentation agent suspended in solution, which may allow more rapid sedimentation with greater portioning of the target of interest.

Suitable sedimentation agents may be, for example, polymers. Suitable polymers may be, for example, biopolymers, synthetic polymers, modified biopolymers, or some combination thereof. Suitable biopolymers may be, for example, polysaccharides and polypeptides. In various aspects, the sedimentation agent is a biopolymer. In certain aspects, the biopolymer is a polysaccharide. In further aspects, the polysaccharide is selected from the group consisting of a starch, dextran, cellulose, chitin, xanthum gum, a glycosaminoglycan, and combinations thereof. In still further aspects, the glycosaminoglycan is selected from the group consisting of heparin, heparin sulfate, chondroitin sulfate, and combinations thereof. In other aspects, the biopolymer is a polypeptide. In certain aspects, the polypeptide is selected from the group consisting of albumin, collagen, fibrinogen, immunoglobulin, and combinations thereof.

Suitable synthetic polymers may be, for example, polyoxyethylene, polyvinylpyrrolidone, polylactic acid, polyglycolic acid, and polydioxanone. More particularly, the polyoxyethylene polymer may be, for example, polyethylene glycol (PEG) and polyethylene oxide (PEO). Polyvinlypyrrolidine may be used, for example, to coat silica particles for Percoll density gradient cell separation.

Suitable modified biopolymers may be, for example, hydroxyethyl starch and hydrolyzed collagen (e.g., gelatin). More particularly, the polysaccharide biopolymers may be, for example, starches such as, for example, amylase and amylopectin, dextran, cellulose, chitin, xanthum gum, and glycosaminoglycans such as, for example, heparin, heparin sulfate, and chondroitin sulfate. Other suitable modified biopolymers may be, for example, hydrolyzed collagen-gelatin, Ficoll, and hydroxyethyl starch derivatives. Yet other suitable modified biopolymers may be, for example, oligomers and small molecules such as, for example, cyclodextrins, and the iodinated contrast media (e.g., diatrizoate, iopamidol, iohexol, ioxilan, iopromide, iodixanol, and ioxaglate). Diatrizoate, more commonly known as HYPAQUE, is used in the FICOLL-HYPAQUE density gradient cell separation media. FICOLL is a epichlorohydrin crosslinked polysaccharide. Other suitable ethylene oxide modified starches may be, for example, hydroxyethyl starch (HES) and pentastarch, its related smaller molecular weight relative. The blood thinner heparin/heparin sulfate may be used to induce RBC sedimentation, which is contrary to its anti-platelet blood-thinning action, and thus is a suitable sedimentation agent. Suitable polypeptide biopolymers may be, for example, albumin, collagen, fibrinogen, and immunoglobulins (e.g., IgG, IgM, IgA, IgE, IgD, and combinations thereof). The immunoglobulins referred to herein are not anti-RBC or anti-target cell immunoglobulins, but rather mixed immunoglobulins available from plasma donations that induce RBC rouleaux formation at sufficiently high concentrations.

In certain aspects, the ALISA comprises a plurality of sedimentation agents. The selection of the sedimentation agents is dependent on a variety of variables that one skilled in the art can readily optimize. When a plurality of sedimentation agents are used, they can be present in a variety of ratios to advantageously optimize the method of isolating a target using the antibody-linked immuno-sedimentation agent. For instance, suitable sedimentation agents can be produced from a mixture of approximately 20 g of polyethylene glycol-PEG-20,000, 70 g of dextran-Dextran-70, or 180 g of hydroxyethyl starch-Hetastarch.

Antibodies

The antibody-linked sedimentation agent of the present disclosure may include at least one antibody linked to at least one sedimentation agent. In some aspects, two or more antibodies (or different types of antibodies) directed to different antigens may be linked to the at least one sedimentation agent. In another aspect, at least two antibodies directed to different antigens may be linked to two or more different sedimentation agents.

Selection of the antibody is at least in part dictated by the sedimentation agent. Antibodies may be directly or indirectly linked to the sedimentation agent, as further detailed herein, by a non-antigen binding region of the antibody; that is the antibodies are linked to the sedimentation agent in a manner such that the hypervariable, paratope, or antigen binding domain is capable of or free to bind its antigen. Thus, the antibody is not linked to the sedimentation agent by the antigen binding region.

Selection of the antibody is also at least in part dictated by the target or unwanted component to which the antibody binds. For example, antibody of the ALISA may be directed to a target antigen or a non-target antigen. As used herein, a "target antigen" refers to an antigen found on a target that one intends or desires to isolate from a sample. For example, if one intends or desires to isolate a white blood cell from a sample according to the method, a white blood cell antigen that is bound by an anti-white blood cell antibody would represent a target antigen. An antibody that binds a target antigen would be used in a positive selection method, for example.

As used herein, a "non-target antigen" refers to an antigen found on an "unwanted" component that is bound by the antibody of the ALISA. Thus, one skilled in the art performing the method may remove or deplete an unwanted component from a sample by using an antibody specific for an antigen on the unwanted component. The unwanted component is then co-sedimented as part of the ALISA-rouleaux complex and the target that one intends or desires to isolate from the sample remains in another layer. An antibody that binds a non-target antigen would be used in a negative selection method, for example.

The concentration of the antibody used to prepare the ALISA is dependent on a variety of variables that one skilled in the art can optimize for its intended purpose. The concentration of the antibody used to prepare the ALISA may depend, for example, on the concentration of sedimentation agent used to prepare the ALISA, the ratio of sedimentation agent to antibody, and/or the method used to link the antibody to the sedimentation agent, among others.

The ALISA includes at least one antibody (or one type of antibody). Because the antibody is directed to a target antigen or non-target antigen, the molecule bound by the antibody becomes associated with the ALISA through direct association with the antibody of the ALISA. The molecule also associates indirectly with the rouleaux/rouleaux networks because of the ALISA-rouleaux/rouleaux network association. This results in the co-sedimentation of the molecule to which the antibody of the ALISA is bound out of the mixture and into the RBC rouleaux layer.

In another aspect, the ALISA may include antibodies directed to different antigens. This aspect may be used, for example, to bind more than one molecule in a sample. This aspect may also be used, for example, to link antibodies directed to different antigens of the same molecule.

Antibodies used to prepare the ALISA may be of many different forms. Suitable antibodies may be monoclonal and polyclonal antibodies. Both monoclonal and polyclonal antibodies of any type or subtype may be used such as, for example, IgM, IgG (IgG1, IgG2, etc.), IgA, IgD, and IgE. Other suitable antibodies include chimeric antibodies, bifunctional antibodies, bispecific antibodies, intact antibodies, and antibody fragments. Suitable antibody fragments include antigen binding (variable) regions, antibody light chains, Fab, F(ab')$_2$, and F(ab').

Antibodies may originate from human or any other species such as, for example, goat, rabbit, sheep, rat, mouse, chicken, donkey, and camel. Suitable antibodies may also be partially humanized through the chemical linking of human antibody components to other species' antibodies. Suitable antibodies may also be produced using recombinant protein expression methods.

Linking and Attaching Antibodies to the Sedimentation Agent to Prepare ALISA

As previously noted above, antibodies are linked or attached to the sedimentation agent in the ALISA of the present disclosure. The antibodies may be directly or indirectly linked to the sedimentation agent. The nature of attachment may depend on a number of potential variables such as, for example, the chemical make-up of the sedimentation agent and/or the antibody itself. The antibody may be linked to the sedimentation agent by Fc regions, hinge regions, light chain constant ($C_L$) regions, heavy chain ($C_H^1$) regions, light chain ($C_L$) regions and heavy chain ($C_H^1$) regions, heavy chain ($C_H^2$) regions, heavy chain ($C_H^3$) regions, or some combination thereof (if, for example, a number of different antibodies are used).

The act of attaching the antibody to the sedimentation agent may be carried out using methods or techniques generally known in the art. Conjugation chemistry, for example, is a suitable process for directly linking or attaching antibodies to the sedimentation agents. Suitable conjugation methods are well known to those skilled in the art. For example, Greg T. Hermanson, Bioconjugate Techniques (2d ed. 2008) provides numerous experimental protocols available for the conjugation of various agents to polypeptides such as antibodies. These conjugation protocols are incorporated herein by reference for this purpose.

Conjugation chemistry may utilize several different functionalities on the antibody polypeptides. Linkages may be made through sulfide bonds to cysteine residues on the antibodies with disulfide bond formation. Linkages may also be made through amine groups on lysine residues or on the amino-terminus of the polypeptide. This forms amide bonds from the starting amine groups condensing with various reactive carbonyl moieties such as, for example, acidic anhydrides or acyl chlorides. Linkages may also be made through alcohol functionalities on tyrosine or threonine residues of the antibody to form esters after reacting with various reactive carbonyl moieties. Conjugation chemistry may also use the carboxy terminus of the polypeptide to form esters and amides. All of these methods of linking the anti-target antibodies to the sedimentation agent are well established and available as kits from commercial vendors.

Another suitable method for linking and attaching the sedimentation agent and the antibody is by non-covalent binding. Non-covalent binding is an indirect method of linking antibodies to the sedimentation agent. Suitable non-covalent methods to attach the antibody to the sedimentation agent may use, for example, binding of biotin to avidins. Avidins are tetrameric proteins that tightly bind four biotin molecules. Biotin, also called vitamin B7, may be attached using the standard chemistry kits by biotinylation. Similarly, streptavidin and avidins may be linked using protein chemistry linking kits. Streptavidin may be linked to the sedimentation agent. This allows for the versatile use of a generic streptavidin or avidin conjugated ALISAs, such as, for example, HES-SE (hydroxyethyl starch-streptavidin), to many different biotinylated antibodies. A single incubation step allows for the non-covalent binding of the biotinylated-antibody to the streptavidin-conjugated sedimentation agent. Suitable biotinylated antibodies may be, for example, biotin-anti-CD4, biotin-anti-CD8, or biotin-anti-CD56.

Another suitable indirect method of linking or attaching antibodies to a sedimentation agent may use a spacer molecule. A spacer molecule provides additional distance or separation between the sedimentation agent and an antibody, or also, for example, to limit possible steric hindrance that may otherwise interfere with antibody-antigen interaction. Suitable peptide spacer molecules may be, for example, chemical spacers, amino acid spacers, peptide spacers, or some combination thereof. (See e.g., Veronese and Morpurgo, Il Farmaco 54: 497-516 (1999)).

ALISA Method

One aspect of the present disclosure includes methods of isolating a target from a sample using an antibody-linked immuno-sedimentation agent (ALISA). The methods include forming a mixture comprising a sample comprising at least one target, an ALISA, and red blood cells and recovering a target from the mixture. The ALISA includes at least one sedimentation agent and at least one antibody linked or attached to the sedimentation agent. The mixture is then incubated under conditions sufficient to form a rouleaux. According to the various methods described herein, a rouleaux is formed by adsorption of the at least one sedimentation agent onto the red blood cells of the rouleaux. Following the incubation, a target is recovered using methods generally known in the art and/or as further described elsewhere herein.

FIG. 1 is an illustration showing at least four components used in the methods of the present disclosure. The components illustrated in FIG. 1 include red blood cells ("erythrocyte matrix"), targets (open circles), unwanted components (hatched circles), and the ALISA (i.e., sedimentation agent with linked antibodies). In this illustration the antibody of the ALISA is specific to an antigen on an unwanted component(s). It is to be noted, however, that in an alternative embodiment, the antibody of the ALISA may be specific to an antigen on a wanted or desired target (as further detailed elsewhere herein). As used herein, a "target" is a molecule or cell in a sample that is wanted or desired to be isolated from a sample. As used herein, an "unwanted component" is a molecule or cell in a sample from which a target is to be separated.

The sample comprising at least one target, ALISA, and red blood cells may be added in any order to form the mixture. For example, ALISA may be added to a sample prior to adding red blood cells. Alternatively, red blood cells may be added to the sample prior to adding ALISA. In yet another embodiment, the target may be part of a sample that includes RBCs, and thus further addition of RBCs may not be needed (or further addition of RBCs may be optional). In one aspect, the ALISA is prepared prior to its addition to form the mixture (that its, the antibody is first attached to the sedimentation agent). In another aspect, a sample such as, for example, blood, may contain red blood cells and ALISA is added to the sample containing red blood cells to form the mixture. In another aspect, ALISA and red blood cells may be mixed prior to addition of a sample to form the mixture.

The mixture is then incubated for a sufficient time to allow the formation of red blood cell rouleaux and for the ALISA antibodies to bind their antigens. In another aspect, the mixture is further incubated for a sufficient time to allow the formation of red blood cell rouleaux networks and for the ALISA antibodies to bind their antigens. According to the various methods described herein, a rouleaux is formed by adsorption of the at least one sedimentation agent onto the red blood cells of the rouleaux. In various aspects, the at least one antibody is linked to the at least one sedimentation agent prior to forming the mixture. Incubation times may vary depending on, for example, the RBC number and/or concentration, the concentration of the antibody-linked sedimentation agent, the concentration of the sedimentation agent(s) used to prepare the ALISA, the concentration of antibodies in the ALISA, the combination of sedimentation agents used to prepare the ALISA when more than one sedimentation agent is used, the molecular weight of the sedimentation agent, the ionic strength of the mixture, the concentration of the target/unwanted component to be bound by the antibody of the ALISA, the composition of the sample, the pH, and/or the temperature, among others, and thus, one or more of these parameters may be optimized by one of skill in the art for a specific condition. (See e.g., Maeda and Shiga, Biochim. Biophys. Acta. 843: 128-136 (1985)). Suitable times may be, for example, from about 10 minutes to about 120 minutes.

Figure 2:
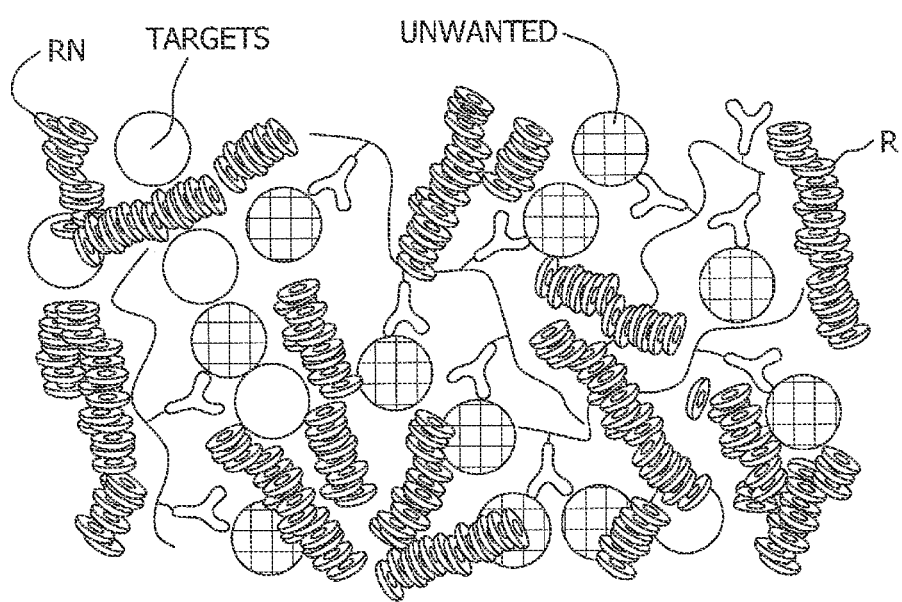
FIG. 2 is an illustration of a mixture showing antibodies of the ALISA bound to unwanted components (hatched circles), rouleaux (R) and rouleaux networks (RN), and the target (open circles) in a negative selection method in which unwanted components are bound to ALISA and co-sediment in the rouleaux layer.

FIG. 2 is an illustration of a mixture showing antibodies bound to unwanted components (hatched circles), rouleaux and rouleaux networks, and the target (open circles). The illustration shown in FIG. 2 represents a negative selection method in which unwanted components are bound to the antibody of the ALISA. In an alternative embodiment, however, a positive selection method may be used wherein a target is bound to the antibody of the ALISA (not illustrated).

Figure 3:
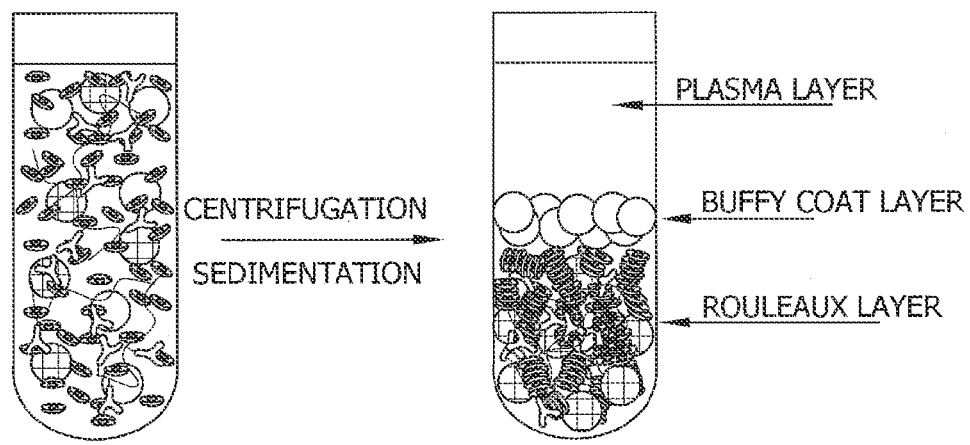
FIG. 3 is an illustration showing centrifugation/sedimentation of a mixture where antibodies of the ALISA are bound to unwanted components (hatched circles), rouleaux and rouleaux networks, and the target (open circles) sediment to the buffy coat layer in a negative selection method in which unwanted components are bound to ALISA and co-sediment in the rouleaux layer.

The resulting incubated mixture is then subjected to a separation technique of some kind (e.g., phase separation) to separate the target from the unwanted component(s) and/or the mixture. In one embodiment, separation is achieved using a sedimentation method to pellet the target or unwanted component that is bound to the ALISA-rouleaux/rouleaux network complex. FIG. 3 is an illustration showing centrifugation/sedimentation of a mixture according to the present disclosure. Prior to centrifugation/sedimentation, the components of the mixture are randomly distributed within the reaction tube. Upon centrifugation/sedimentation, the components of the mixture are separated into a plasma layer, a buffy coat layer, and a rouleaux layer. As used herein, a "rouleaux layer" refers to the layer formed by rouleaux and rouleaux networks. The rouleaux layer contains red blood cells and the ALISA bound to the molecule having the antigen to which the antibody of the ALISA is directed. In a positive selection method, the target to be isolated would be bound to the ALISA and pellet in the rouleaux layer. In a negative selection method, the target to be isolated would be in either the buffy coat layer or the plasma layer and unwanted component(s) would be bound to the ALISA. Once separated into the noted layers, the target may be isolated or collected using methods known in the art (e.g., decanting, filtration, extraction, precipitation, cell lysing, etc.).

The concentration of the ALISA in the mixture is dependent on a variety of variables that one skilled in the art can optimize to achieve the desired separation (and/or separation rate). A suitable concentration of the ALISA may be between about 0.1 g/dL to about 10 g/dL. The optimal concentration may, for example, depend on the molecular weight of the ALISA. For a more rapid isolation, for example, one skilled in the art may increase the ALISA concentration to increase the rate of rouleaux formation and/or increase the rate of target bound by the antibodies of the ALISA. For a slower isolation, for example, one skilled in the art may decrease the ALISA concentration to slow the rate of rouleaux formation and/or decrease the rate of target binding by the antibodies of the ALISA.

The number or concentration of red blood cells in the mixture is dependent on a variety of variables that one skilled in the art can optimize. A suitable concentration of red blood cells may be between about 0.5 to about 10 million red blood cells per microliter. For a more rapid isolation, for example, one skilled in the art may increase the red blood cell concentration to increase the rate of rouleaux and/or rouleaux network formation. For a slower isolation, for example, one skilled in the art may decrease the red blood cell concentration to slow the rate of rouleaux and/or rouleaux network formation. In this regard, it is to be noted, however, that in some instances red blood cells may need to be added to the mixture separately, while in other instances they are simply present as part of the sample that contains the target or unwanted component.

Suitable pH of the mixture may be between about 5.4 to about 9.4. Particularly suitable pH of the mixture may be between about 7.3 to about 7.5. Suitable temperatures may be between about 0° C. to about 45° C. Particularly suitable temperatures may be between about 18° C. to about 25° C.

The ratio of antibodies to targets (wanted or unwanted components) in the ALISA may be optimized by one skilled in the art. Typically antibody concentrations are titrated down to be in a significant excess relative to the target concentrations. This excess concentration optimizes target isolation. Use of a higher antibody concentration beyond the titration threshold concentration may provide little gain in target isolation for additional use of costly antibody reagents. Titration adjustments to the antibody concentration of the ALISA ratio can be optimized by one skilled in the art.

In certain aspects, the present disclosure is directed to a method of isolating a target from a sample. The method comprises forming a mixture comprising a sample, an antibody-linked immuno-sedimentation agent and red blood cells, wherein the antibody-linked immuno-sedimentation agent comprises at least one sedimentation agent selected from the group consisting of polyethylene glycol, dextran, and hydroxyethyl starch; and at least one antibody linked to the at least one sedimentation agent by a non-antigen binding region of the antibody, wherein the antibody is selected from the group consisting of an anti-CD3 antibody, an anti-CD19 antibody, an anti-insulin antibody, an anti-CD34 antibody, an anti-CD4 antibody, an anti-CD14 antibody, an anti-CD16 antibody, an anti-CD19 antibody, an anti-CD20 antibody, an anti-CD36 antibody, an anti-CD56 antibody, an anti-CD123 antibody, an anti-TCRγ/δ antibody, an anti-glycophorin A antibody, and an anti-GP120 antibody; incubating the mixture under conditions sufficient to form a rouleaux and allow the antibody to bind to an antigen present in the mixture; and recovering a target from the mixture.

Rouleaux and Rouleaux Networks

Figure 4A:
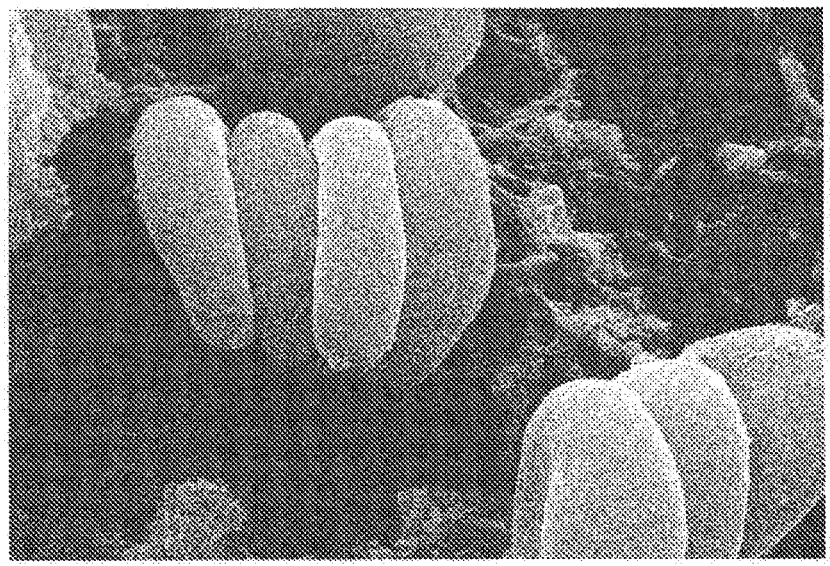
FIG. 4A is a scanning electron micrograph showing red blood cells stacking together to form a rouleaux.
Figure 4B:
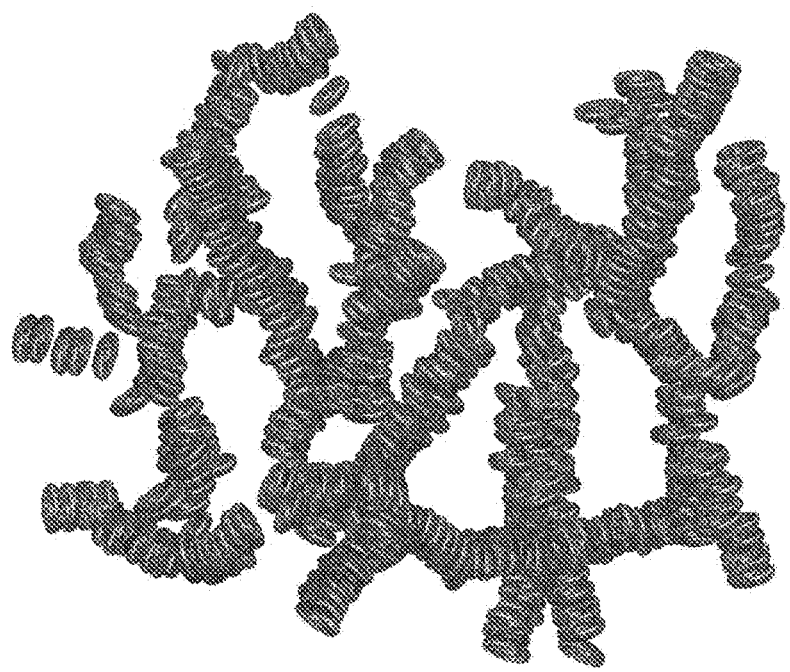
FIG. 4B is a drawing showing red blood cell rouleaux and red blood cell rouleaux networks.

In one aspect of the method, the mixture is incubated under conditions sufficient to form rouleaux and for the ALISA antibodies to bind their antigens. In another aspect of the method, the mixture is incubated under conditions sufficient to form rouleaux networks and for the ALISA antibodies to bind their antigens. Without being bound to any particular theory, the process of rouleaux, or rouleaux network, formation is believed to begin with a sedimentation agent adsorbing to the surface of the RBCs. The adsorption of the sedimentation agent onto the RBCs induces a reversible process of stacking of the RBCs to form rouleaux. See, FIG. 4A. Rouleaux may then bridge with other rouleaux to form rouleaux networks. See, FIG. 4B. FIG. 4B shows individual rouleaux interacting with other rouleaux to form rouleaux networks. RBCs in the form of rouleaux and rouleaux networks lead to a settling out of RBCs from the suspension.

Figure 5:
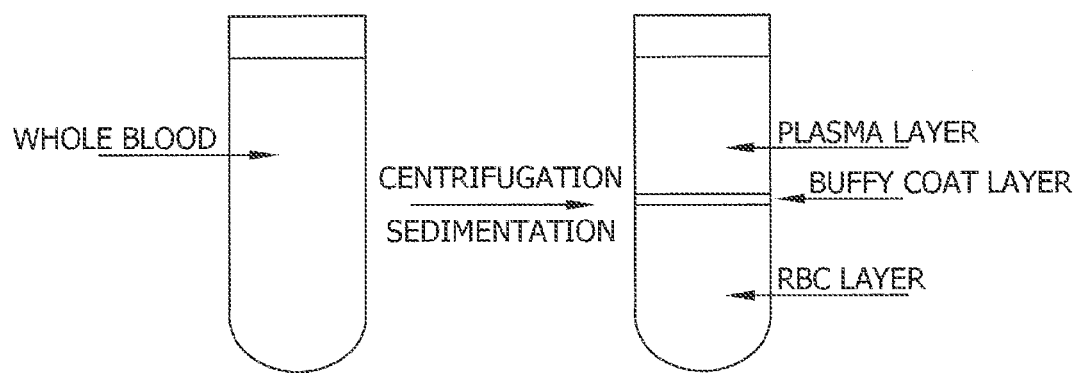
FIG. 5 is an illustration showing centrifugation/sedimentation of whole blood.
Figure 6:
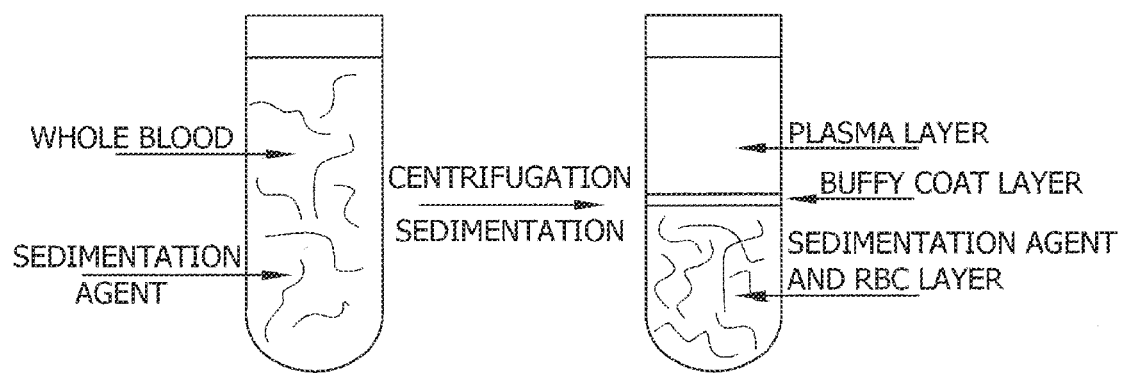
FIG. 6 is an illustration showing centrifugation/sedimentation of whole blood into which a sedimentation agent is added.

RBCs will sediment naturally (but more slowly) on their own without the addition of a sedimentation agent. FIG. 5 is an illustration showing centrifugation/sedimentation of whole blood. Following centrifugation/sedimentation, whole blood separates into a plasma layer, a buffy coat layer, and a red blood cell layer. Conventionally, sedimentation agents may be added to whole blood to enhance sedimentation of RBCs. FIG. 6 is an illustration showing conventional centrifugation/sedimentation of whole blood into which a sedimentation agent is added. Following centrifugation/sedimentation, whole blood separates into a plasma layer, a buffy coat layer, and a sedimentation agent/red blood cell layer. This conventional approach is distinctly different from the process of the present disclosure, most notably because the sedimentation agent lacks an antibody linked thereto (i.e., no ALISA is present in the mixture).

Figure 7:
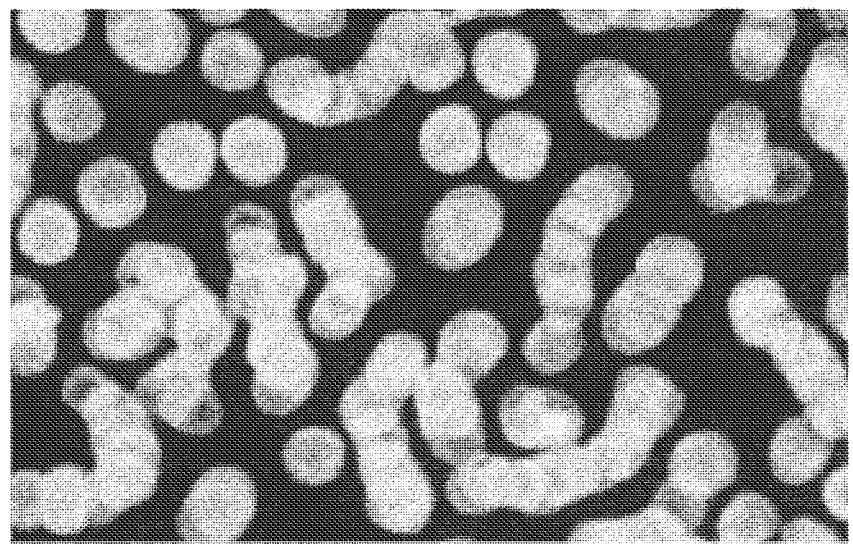
FIG. 7 is a photomicrograph showing RBC rouleaux.
Figure 8:
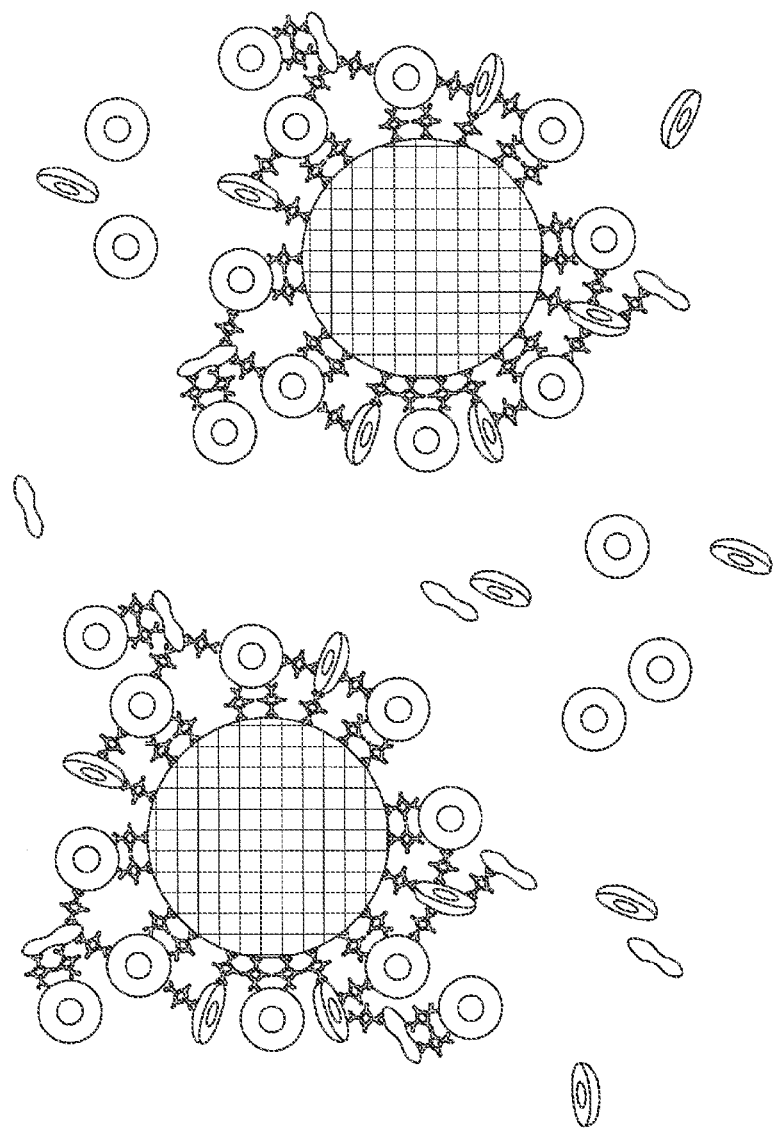
FIG. 8 is an illustration of a prior art method using RBC immunorosetting and a tetrameric antibody complex to isolate a target (hatched circle) from a sample.

The process of the present disclosure, which uses rouleaux and rouleaux network formation, is also to be distinguished from processes that involve or use rosettes or immunorosettes, which are also formed by RBCs and used in other prior methods. Rosettes are aggregates of RBCs, not stacked RBCs as found in rouleaux and rouleaux networks. Immunorosettes are antibody-mediated rosettes. Immunorosettes enhance RBC aggregation by linking RBCs with each other and with the target using antibodies directed to RBCs and targets. FIG. 7 is a photomicrograph of RBC rosettes. The RBC aggregates that form rosettes show a more clumpy structure as compared to the stacks formed by RBCs in rouleaux and rouleaux networks (FIG. 7). FIG. 8 is an illustration of a prior art method using immunorosetting to isolate a target from a sample. Unlike the ALISA method, in the immunorosetting method, an anti-RBC antibody (for example, anti-glycophorin A), an anti-target antibody, and antibodies directed to the anti-RBC antibody and anti-target antibody are used to link the anti-RBC antibody and anti-target antibody together into a tetrameric antibody complex (TAC).

Figure 9:
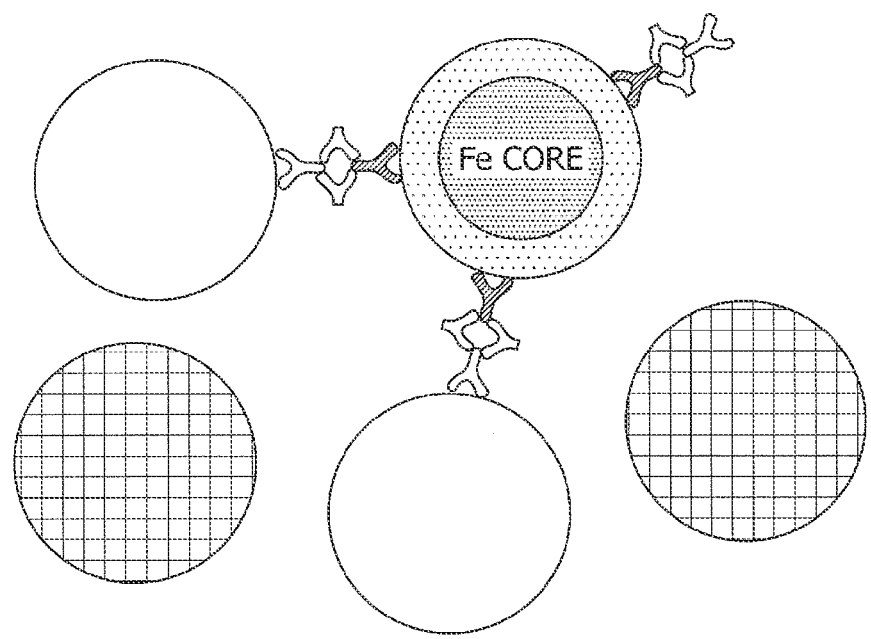
FIG. 9 is an illustration of a prior art method using RBC immunorosetting and a tetrameric antibody complex combined with dextran-coated magnetic particles to isolate a target from a sample.
Figure 10:
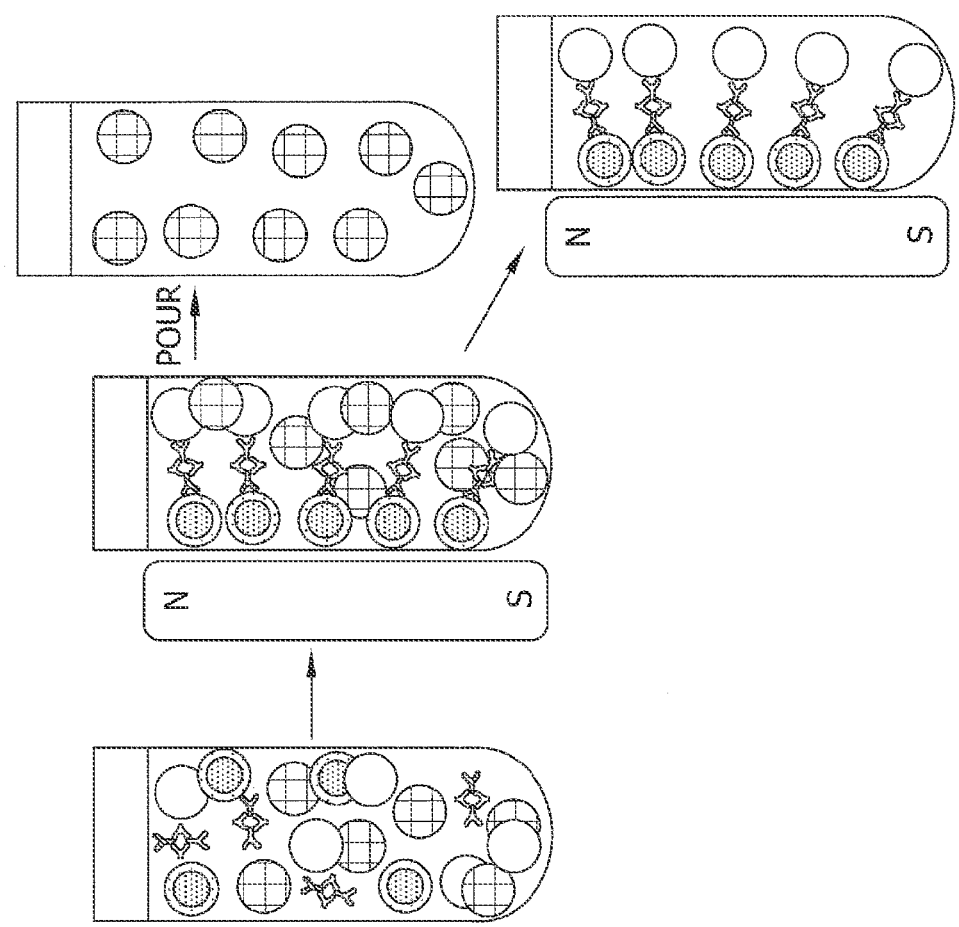
FIG. 10 is an illustration of a prior art method using RBC immunorosetting and a tetrameric antibody complex combined with dextran-coated magnetic particles and application of a magnetic field to isolate a target from a sample.
Figure 11:
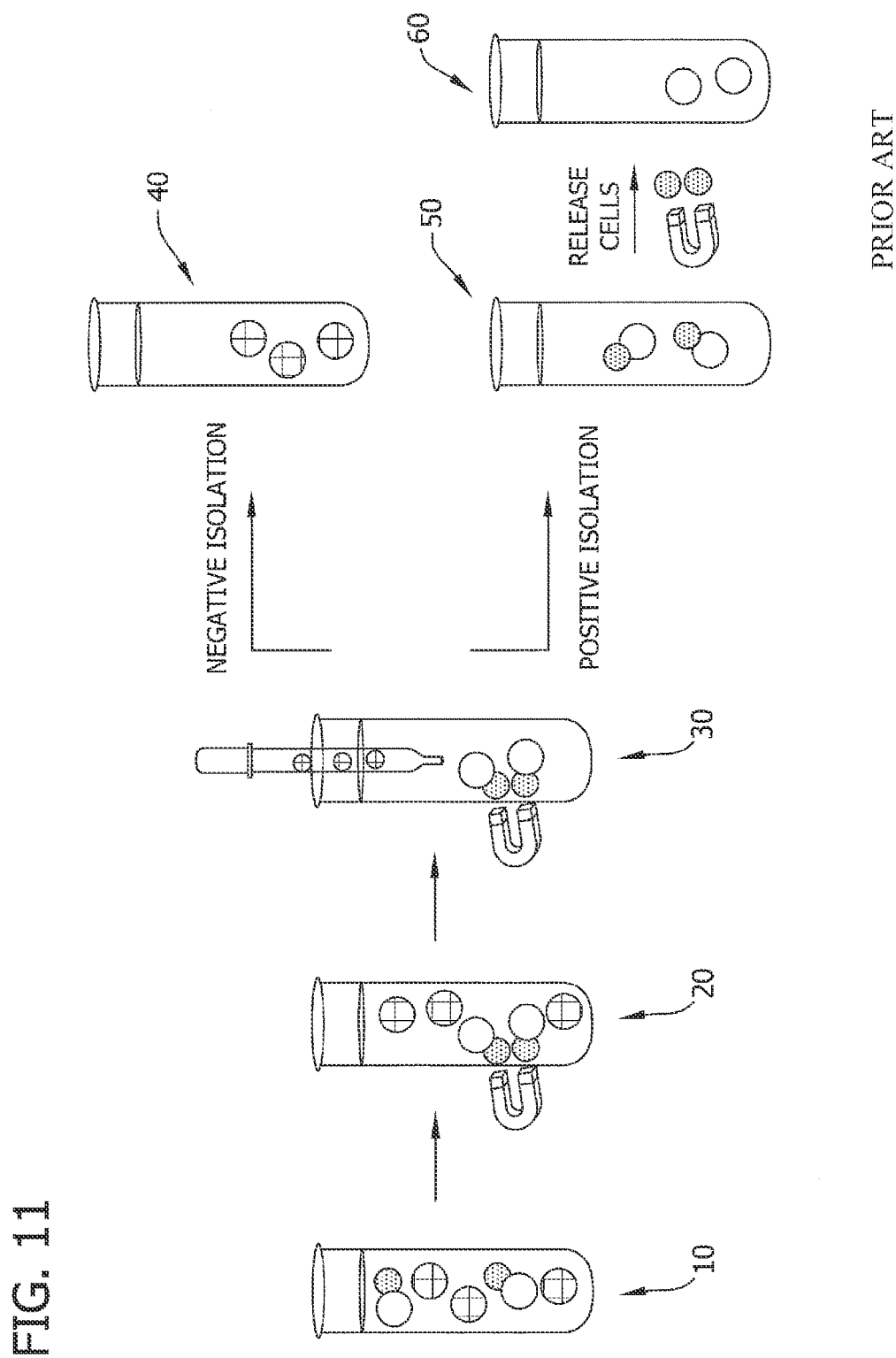
FIG. 11 is an illustration of a prior art method using RBC immunorosetting and a tetrameric antibody complex combined with dextran-coated magnetic particles and application of a magnetic field to isolate a target from a sample by positive selection followed by release of cells and negative selection.

The immunorosetting method may also use dextran-coated magnetic particles and anti-dextran antibodies that bind via the FAT region of the antibody to the dextran coating on the magnetic particles. (See, FIG. 9.) The magnetic beads are used in combination with the anti-RBC antibodies and linking antibodies to form the tetrameric antibody complex (TAC). The TAC links red blood cells to a target and/or magnetic particles and/or other red blood cells to form RBC immunorosettes. As illustrated in FIGS. 10 and 11, the mixture is subjected to a magnetic field. While the magnetic field is applied, any components not bound to the magnetic particles may be poured off. As illustrated in FIG. 11, this method can be used for positive and negative selection methods.

Samples

The sample used in the process of the present disclosure may be any solution or mixture having a target one wishes to isolate from the sample. Suitable samples may be, for example, blood, bone marrow, peripheral blood stem cell isolates, bone-marrow aspirates, buffy-coat layer, leukapheresis isolates, plasmapheresis isolates, cell suspensions, cell culture media, cell mixtures, cell homogenates, pancreas isolates, organ homogenates (e.g., liver, brain, kidney, pancreas, lung, muscle, adipose tissue, spleen, lymph node, pituitary, thyroid, parathyroid, adrenal, ovarian, testicular, uterine, heart, or tumor cells), saline solutions, Ringer's solution, lactated Ringer's solution, phosphate buffered saline solutions, viral culture media, oocyte, sperm, gamete mixtures, or some combination thereof. In one aspect, the blood may be, for example, whole blood, blood plasma, platelet-rich plasma, fractionated blood, packed red blood cells, umbilical cord blood, bone marrow, stem cell blood isolates, or some combination thereof. A cell mixture or cell suspension may be, for example, cell cultures, cell homogenates, a bacteria-containing sample, a multicellular organism-containing sample, an amoeba-containing sample, and other cell-containing mixtures and suspensions, or some combination thereof. The sample may also be, for example, a cell-free mixture such as, for example, a protein-containing sample, a polypeptide containing sample, a nucleotide-containing sample, a polysaccharide-containing sample, a lipid particle-containing sample, a micelle-containing sample, a virus-containing sample, a viroid-containing sample, a platelet-containing sample, a molecule-containing sample, or some combination thereof.

Red Blood Cells (RBCs)

The method of the present disclosure using ALISA depend on the formation of RBCs into rouleaux and rouleaux networks, and thus RBCs are required in the method. Red blood cells (or erythrocytes) are a type of blood cell that flow through the circulatory system to deliver oxygen to the body tissues. RBCs may originate from the sample such as, for example, blood. In certain aspects, the blood comprises whole blood, blood plasma, a blood stem cell isolate, platelet-rich plasma, fractionated blood, packed red blood cells, umbilical cord blood, bone marrow, a bone-marrow aspirate, and a buffy-coat layer. Alternatively or additionally, RBCs may be added to a sample to increase the number of RBCs (such as, for example, a bone marrow aspirate). Alternatively or additionally, RBCs may be added to mixtures lacking or deficient in RBCs (such as, for example, a bacteria-containing sample and a pancreas homogenate).

In some embodiments, the red blood cells comprise endogenous red blood cells. As used herein, "endogenous red blood cells" refers to red blood cells that inherently populate or are found in the sample. A sample that includes endogenous red blood cells may be, for example, whole blood, fractionated blood, umbilical cord blood, and bone marrow. Thus, when whole blood, for example, is used as the sample, the red blood cells populating the whole blood sample represent endogenous red blood cells.

In other embodiments, the method may include adding exogenous red blood cells. As used herein, "exogenous red blood cells" refers to red blood cells that are separately added to a sample (as detailed herein). The optimal amount of added RBCs, if any, depends on the amount of targets and the desired rate of rouleaux and/or rouleaux network formation.

In some embodiments, the added exogenous red blood cells may be autologous red blood cells. As used herein, "autologous red blood cells" refers to red blood cells obtained from or donated by the same species as the endogenous red blood cells contained in the sample. Thus, if the sample is whole blood obtained from a human subject, for example, and exogenous red blood cells are added to the whole blood, the exogenous red blood cells would be autologous red blood cells if the added red blood cells are obtained from a human donor, but not the same individual. "Autologous red blood cells" may optionally refer to red blood cells obtained from or donated by the same species as the origin of the sample solution. For example, if the sample is a solution of human pancreatic cells to which exogenous red blood cells are added, the exogenous red blood cells would be considered autologous red blood cells if the added red blood cells are from a human donor, but not necessarily the same human donor.

In other embodiments, the added exogenous red blood cells may be homologous red blood cells. As used herein, "homologous red blood cells" refers to exogenous red blood cells obtained from or donated by the same individual. Thus, homologous red blood cells are autologous red blood cells obtained from or donated by the same individual. Thus, if the sample is whole blood obtained from a human individual, for example, and red blood cells are added, the added red blood cells would be homologous red blood cells if the added red blood cells are obtained from the same human individual.

In yet other embodiments, the added exogenous red blood cells may be heterologous red blood cells. As used herein, "heterologous red blood cells" refers to red blood cells obtained from or donated by a different species. Different species have different inherent rates of sedimentation of their RBCs, and the use of RBCs originating from different species may affect the immuno-sedimentation. The use of faster rouleaux forming RBCs, for example, may accelerate the rate of rouleaux and/or rouleaux network formation, and thus accelerate the sedimentation rate. For example, antelope, horse, and other athletic animals have RBCs that form rouleaux more rapidly than human and cattle RBCs and may enhance the sedimentation rate, allowing for more rapid sedimentations. Suitable species to donate heterologous red blood cells may be, for example, mammalians, for example, cattle, horse, goat, rabbit, sheep, dog, rat, mouse, antelope, and cat, avians, for example, chicken, quail, turkey, duck, goose, or some combination thereof.

RBCs for the ALISA methods may also come from packed RBCs collected from human blood donors. The packed RBCs only need to be re-suspended into the sample.

Targets

A target may be any molecule, cell, etc. of interest in a sample that is desired or wanted to be isolated or separated from other components of the sample, as previously described. The target may be, for example, multicellular organisms, single-cell organisms, cells, subcellular components, cellular fragments, virus and virus-like targets, membrane-bound and lipid particles, macromolecules, nucleic acids, and proteins. Multicellular organisms may be, for example, worms, flukes, and parasites. Single-cell organisms may be, for example, bacteria, single-cell eukaryotes, protozoa, malaria, trypanosomes, and amoebae. Cell collections may be, for example, pancreatic islets, bone marrow and stem cell aggregates, hepatocytes, tumor metastases, and parafollicular cells (C-cells). Subcellar components may be, for example, mitochondria, nuclei, nucleoli, centrioles, chloroplasts, lysosomes, kinetoplasts, endosomes, ribosomes, and storage vesicles. Cellular fragments may be, for example, apoptotic bodies, platelets, and exosomes. Virus and virus-like targets may be, for example, DNA and RNA viruses, viroids, and phages. Membrane-bound and lipid particles may be, for example, liposomes, lipoproteins (chylomicrons, VLDL, IDL, LDL, HDL), and micelles. Macromolecules and proteins may be, for example, any compound or motif that can be targeted by an antibody including proteins, peptides, polypeptides, polysaccharides, DNA, RNA, nucleic acid-like macromolecules (e.g., peptide nucleic acids, locked nucleic acids, and other modified nucleic acid-like molecules), synthetic polymers, oligomers, lipids, sugars, glycosaminoglycans, and heterocomplexes of these constituents.

Blocking Agents

The method may further include the addition of a blocking agent. As used herein, a "blocking agent" refers to any agent used to avoid or prevent non-specific binding of the antibodies. Blocking agents may be, for example, a protein colloid such as, for example, human albumin, bovine serum albumin, or fetal bovine serum, immunoglobulins, anti-CD16 antibodies, anti-Human CD32 (FcγRII), Fc receptor antibodies, or some combination thereof.

Recovering a Target from the Mixture

Recovery of the wanted or desired target from unwanted components may involve either separating a target bound by the ALISA-rouleaux/rouleaux network complex or separating a target from the mixture when the unwanted component is bound by the ALISA-rouleaux/rouleaux network complex. Separation may be achieved using a variety of techniques, all generally known in the art. Suitable techniques may be, for example, sedimentation in response to gravity (1×g) or centrifugal force created by centrifuging the mixture. (See e.g., FIG. 3). Sedimentation of the sample may be by the force of gravity (1×g) and by centrifugation. Thus, the present disclosure is intended to include separation at any gravity or centrifugal force.

Another suitable technique may be, for example, density separation using either a continuous or discontinuous density gradient. In density separation, the mixture is layered over a buoyant density solution (such as, for example, FICOLL HYPAQUE) and centrifuged. The antibody bound molecule-ALISA-rouleaux/rouleaux network complex pellet and the remaining unbound components of the sample collect at the interface between the buoyant density solution and the antibody bound molecule-ALISA-rouleaux/rouleaux network complex. If a positive selection method is employed, for example, the antibody bound molecule (target) bound to the ALISA would pellet in the ALISA-rouleaux/rouleaux network complex. The target may be further separated from the target-ALISA-rouleaux/rouleaux network complex by a variety of techniques. Suitable techniques may be, for example, lysis of the red blood cells and separation and/or purification of the target from the lysate, disruption of the antibody-antigen binding, and other methods used by one skilled in the art. If a negative selection method is used, for example, the unwanted component(s) would be bound by the antibody of the ALISA an unwanted molecule and would pellet in the ALISA-rouleaux/rouleaux network complex. In a negative selection method, the wanted or desired target would remain in a layer or layers above the pelleted unwanted molecule-ALISA-rouleaux/rouleaux network complex. The wanted or desired target may then be removed from layer(s) above the pelleted unwanted molecule-ALISA-rouleaux/rouleaux network complex by a variety of techniques generally known in the art.

Figure 12:
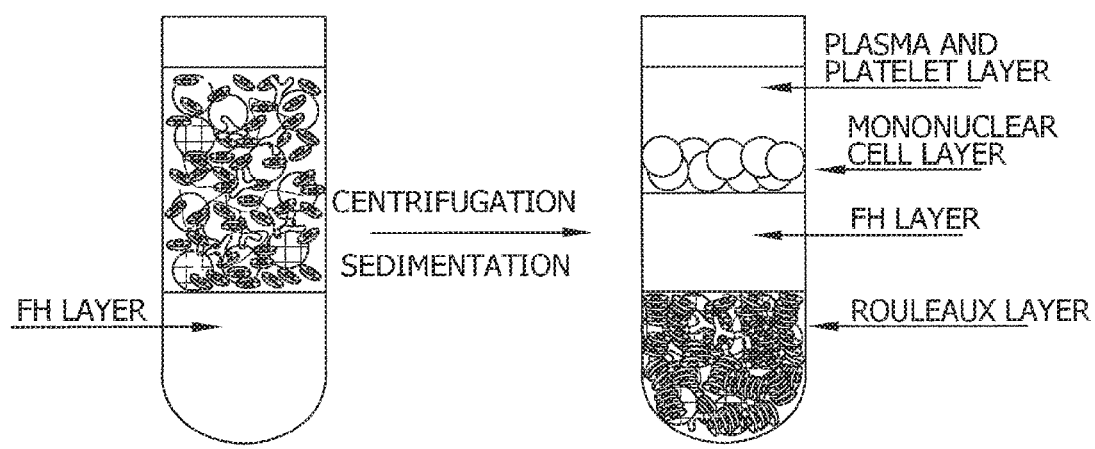
FIG. 12 is an illustration showing sedimentation of ALISA-rouleaux using FICOLL HYPAQUE (FH Layer).
Figure 13:
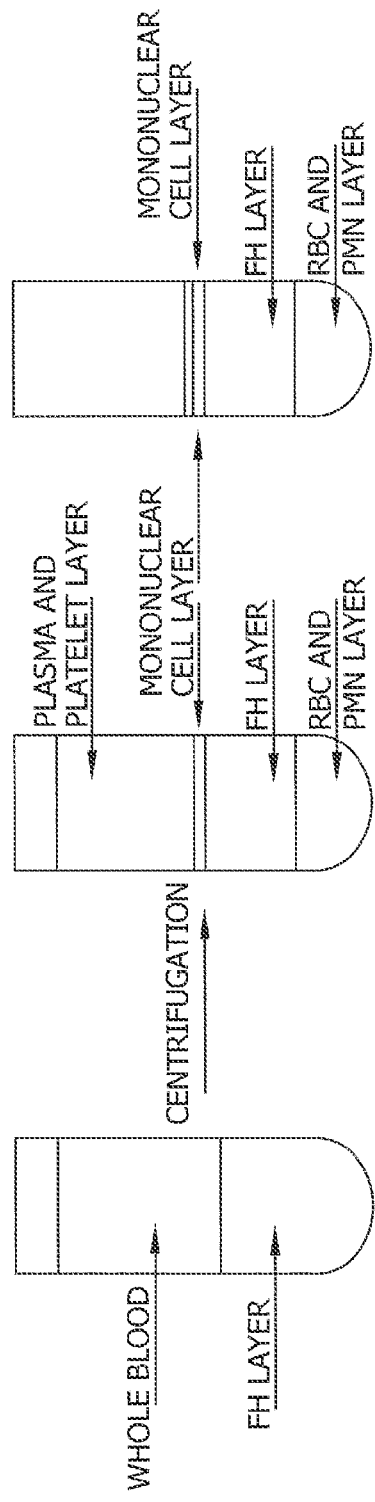
FIG. 13 is an illustration showing centrifugation/sedimentation of whole blood in the absence of ALISA using FICOLL HYPAQUE (FH Layer).

FIG. 12 is an illustration showing sedimentation of ALISA-rouleaux using FICOLL HYPAQUE. The mixture is layered over a FICOLL HYPAQUE (FH) layer and subjected to centrifugation/sedimentation. The mixture separates into a plasma and platelet layer, a mononuclear cell layer, an FH layer, and a rouleaux layer. In this illustration, the molecule bound by the antibody of the ALISA would be in the rouleaux layer. For comparison, FIG. 13 is an illustration showing centrifugation/sedimentation of whole blood in the absence of ALISA using FICOLL HYPAQUE. Whole blood is layered over FICOLL HYPAQUE (FH). Following centrifugation, the whole blood separates into a plasma and platelet layer, a mononuclear cell layer, an FH layer, and red blood cell and polymorphonuclear leukocyte (PMN) layer. Other density gradients may also be used such as, for example, Percoll density gradient having colloidal silica particles coated with polyvinylpyrrolidone (for example, with a density of about 1.13 g/ml), sucrose density gradient (for example, about 20% sucrose with a density of about 1.06 g/ml, or metrizamide (for example, with a density of about 1.13 to about 1.14 g/ml). Other density based methods may use, for example, density based floats and beads to separate targets. These floats and beads may be designed to have specific densities to separate targets or unwanted components when used together with the ALISA reagent and method.

In some embodiments, recovering the target may include separating the rouleaux from the mixture. In another embodiment, for example, recovering the target may further include separating the rouleaux networks from the mixture. In yet other embodiments, recovering the target may include subjecting the mixture to at least one of filtration, sedimentation, centrifugation, density gradient centrifugation, a magnetic field, an electrical field, red blood cell lysis, extraction, or combinations thereof.

In another embodiment, recovering the target may include subjecting the mixture to a phase transition or change of at least freezing, thawing, evaporating, boiling, subliming, melting, crystallizing, plasticizing, or combinations thereof.

In other embodiments, recovering the target may include using physical barriers such as frits, filters, and semipermeable barriers alone or in combination with other methods to separate the targets or unwanted components from the mixture.

In other embodiments, recovering the target may include using magnetic and electrical fields alone or in combination with gravity and centrifugation. Alternating current electric fields are known to induce RBC sedimentation. Similarly magnetic fields can induce RBC sedimentation.

In other embodiments, recovering the target may include using chemical reactions of the mixture to crosslink the components in such a way to facilitate their separation. The ALISA may use a sedimentation agent having reactive moieties that can be induced to form a chemical bonds binding the mixture. This chemical reaction can be initiated by temperature, light, free-radicals, or any other method known by one skilled in the art. The resulting chemically linked mixture may then be subjected to any one of the methods discussed above by one skilled in the art.

In this regard, it is to be noted that other separation methods known in the art may be used without departing from the scope of the claims.

Positive and Negative Selection

The methods may be used for positive and negative selection methods. As used herein, "positive" selection" refers to the condition wherein a target is separated from unwanted components using antibodies directed to the target such that the target is sedimented by the ALISA methods. In a positive selection using ALISA of the present disclosure of whole blood for example, an antibody or antibodies directed to a surface antigen of a target cell of interest are linked to the sedimentation agent of the ALISA. Upon rouleaux and/or rouleaux network formation, the target of interest is sedimented into the ALISA-RBC rouleaux/rouleaux network layer away from other unwanted components, which remain in the buffy coat/WBC or plasma layer. If desired, the ALISA-RBC rouleaux/rouleaux network layer may then be removed and/or separated from the co-sedimented target or unwanted component. One method of separating a target or an unwanted component from the ALISA-RBC rouleaux/rouleaux network is to lyse the RBCs. RBCs may be lysed, for example, using cycles of freeze-thaw, homogenization, RBC lysis agents and other techniques generally known in the art.

As used herein, "negative selection" refers to the condition wherein an unwanted component is separated from a target and/or a sample using antibodies directed to the unwanted component such that the unwanted component is sedimented by the ALISA methods. In a negative separation using ALISA of the present disclosure of whole blood for example, antibodies linked to the ALISA are directed to an unwanted component(s). During negative selection, a target remains in the plasma or buffy coat/WBC layer and the unwanted components are sedimented into the ALISA-RBC rouleaux/rouleaux network layer through antigen-binding of the antibodies linked to the sedimentation agent of the ALISA.

As discussed in detail above, if a positive selection method is employed, a target of the target-ALISA-rouleaux/rouleaux network complex may be further separated from the target-ALISA-rouleaux/rouleaux network complex by a variety of techniques. Suitable techniques may be, for example, lysis of the red blood cells and separation and/or purification of the target from the lysate for further use, as previously discussed. If a negative selection method is used, an unwanted component is selected to be removed according to the ALISA method. In a negative selection method, a target would remain in a layer or layers above the pelleted unwanted molecule-ALISA-rouleaux/rouleaux network complex. The target may then be removed, isolated, and/or purified from layer(s) above the pelleted unwanted molecule-ALISA-rouleaux/rouleaux network complex for further use using conventional techniques and methods generally known in the art.

Sedimentation Agents

The selection of the sedimentation agent(s) used to prepare the ALISA is dependent on a variety of variables that one skilled in the art can optimize, as described in detail above.

Antibodies

As described in detail above, the method of the present disclosure uses ALISA including at least one type of antibody directed to a target of interest. Thus, in this aspect, the antibody binds "a target antigen" in the sample. In alternative embodiments, the method of the present disclosure uses ALISA that consists of or consists essentially of at least one type of antibody directed to a target antigen in the sample. In another aspect of the present disclosure, the method of the present disclosure uses ALISA including at least one type of antibody directed an unwanted component contained in a sample. Thus, in this aspect, the antibody binds "a non-target antigen" in the sample. In alternative embodiments, the method of the present disclosure uses ALISA that consists of or consists essentially of at least one type of antibody directed to a non-target antigen in the sample.

In another aspect, the ALISA may include antibodies directed to different antigens. Thus, this aspect may be used, for example, to bind more than one target and/or unwanted component in a sample. This aspect may also be used, for example, to link antibodies directed to different antigens of the same target or unwanted component. In alternative embodiments, the method of the present disclosure uses ALISA that consists of or consists essentially of antibodies directed to different antigens.

Antibodies used to prepare the ALISA may be of many different forms as previously described. Antibodies may originate from human or any other species as previously described.

Linking and Attaching Antibodies to the Sedimentation Agent

As described in detail above, antibodies are linked or attached to the sedimentation agent to prepare the ALISA of the present disclosure. The antibodies may be directly or indirectly linked to the sedimentation agent. The act of attaching the antibody to the sedimentation agent may be carried out using methods or techniques generally known in the art, as previously described.

Alternative or Optional Embodiments

It is to be noted herein that the various listings of possible sedimentation agents, antibodies, targets, separation methods, etc. are provided for illustration and therefore should not be viewed in a limiting sense. One of ordinary skill in the art will recognize a number of other known sedimentation agents, antibodies, targets, separation methods, etc. that may be used in the ALISA and method of the present disclosure. Additionally, the selection of effective or desired combinations of sedimentation agents, antibodies, targets, separation methods, etc. may be recognized or determined by a matter of routine experimentation by one of ordinary skill in the art. However, exemplary combinations may be, for example:

TABLE 1

Exemplary targets and surface markers that can be targeted by ALISA separation methods.

| Target | Marker |
| --- | --- |
| Leukocytes | CD45 |
| Lymphoid cells | CD3 + CD19 |
| Myeloid cells | CD15, CD33, CD33 + CD66b |
| T cells | CD2, CD3, CD6, CD90.1/Thy 1.2-mouse |
| Naïve T cells | CD45RA |
| CD4+ T cells | CD4 |
| CD8+ T cells | CD8 |
| Activated T cells | CD25, CD30, CD169, CD154, CD134-mouse |
| Memory T cells | CD45RO |
| Gamma/delta T cells | TCR-γδ |
| Effector T cells | CD27 |
| Regulatory T cells | CD25 |
| Skin Homing CD4+ T cells | CD4 + CLA |
| B cells | CD19, CD20, CD22 |
| Naïve B cells | CD43 |
| Activated B cells | CD25 + CD30 + CD69 |
| Memory B cells | CD27 + IgG |
| Plasma cells | CD138 |
| NK cells | CD56, CD16 + CD56 |
| Granulocytes | CD15, CD66b |
| Neutrophils/Eosinophils | CD15 + CD16 |
| Myeloid dendritic cell | CD11c, CD141, CD209 |
| Plasmacytoid dendritic cells | CD304 |
| Monocytes | CD14, CD14 + CD16 |
| Stem/progenitor cells | CD34, CD117, CD133 |
| Erythroblasts | CD71 |
| Self-designed-anti-human Antibody | IgG1-mouse |
| Mammary | EpCAM, MUC1 |
| Erythrocytes | Glycophorin A |
| Platelets/Megakaryocytes | CD61 |
| Beta-pancreas islet cells | Insulin |
| Antigen presenting cells | HLA-DR |
| FITC tagged cell | FITC |
| PE tagged cell | PE |
| APC tagged cell | APC |
| Biotin tagged cell | Biotin |
| HIV virions | GP120 |
| Influenza virions | HA |
| Mitochondria | TOM22 |

TABLE 1-continued

Exemplary targets and surface markers that can be targeted by ALISA separation methods.

| Target | Marker |
| --- | --- |
| Protein-GFP tagged | Green Fluorescent Protein |
| Protein-GST tagged | Glutathione S-transferase |
| Transfected cell | CD4 |
| Transfected cell | H-2K-mouse |
| Transfected cell | LNGFR |

Kits

The present disclosure is additionally directed to a kit for isolating a target from a sample. The kit includes, in at least one container, an antibody-linked immuno-sedimentation agent comprising a sedimentation agent and at least one antibody linked to the sedimentation agent. The kit also includes instructions for a method of using the kit, including for example, details for positive and/or negative selection of a target and/or unwanted component, methods of separation, methods for sedimentation, methods of separating the target from a layer, etc. Instructions may include written instructions included with the kit and instructions provided separately. Separate instructions may be provided, for example, on an internet website.

Alternatively, the kit may include two separate containers such as, for example, one for the sedimentation agent(s) and one for the antibody, and additionally containing instructions for linking the antibody to the sedimentation agent to prepare an ALISA.

The disclosure will be more fully understood upon consideration of the following non-limiting Examples.

EXEMPLARY ASPECTS

Example 1

ALISA Preparation using Tricholor-s-triazine

In this Example, ALISA is prepared using Tricholor-s-triazine. Anhydrous sodium carbonate (1 g) is added to 200 ml of anhydrous organic solvent (e.g., acetone, methylene chloride, dimethylsulfoxide, benzene, or 1,4-dioxane). Then, 0.55 g of Trichloro-s-triazine (TsT) is dissolved in the sodium carbonate solution. The sedimentation agent (1 mmol) (approximately 20 g of polyethylene glycol-PEG-20, 000, 70 g of dextran-Dextran-70, or 180 g of hydroxyethyl starch-Hetastarch) is added to the sodium carbonate solution. The solution is then stirred overnight at room temperature. The solution is then filtered. The filtrate is then added to a sufficient amount of a non-polar organic solvent (e.g., of petroleum ether or diethyl ether) (500 ml) to produce an activated sedimentation agent precipitate that is collected by filtration. This activated sedimentation agent precipitate is further cleaned by re-dissolving in the organic solvent, filtering, precipitating in the nonpolar solvent, and filtering. Antibody or antibodies (100 mg, 0.67 µmol (ea)) to be linked to the activated sedimentation agent is dissolved in 20 ml of a buffer (e.g., 0.1M sodium borate at pH 9.4) at a concentration of 5 mg/ml. The activated sedimentation agent (10 µmol per antibody, approximately 0.2 g of PEG-20K, 0.7 g of Dextran-70, or 1.8 g of hydroxyethyl starch-Hetastarch) is slowly added to the reaction solution in an ice-bath (temperature of about 4° C.). The reaction solution is stirred for one hour at 4° C. The final ALISA is isolated or

Example 2

ALISA Preparation using N-Succinimidyl Chloroformate

In this Example, ALISA is prepared using N-Succinimidyl Chloroformate. The sedimentation agent (1 mmol) (approximately 20 g of polyethylene glycol-PEG-20,000, 70 g of dextran-Dextran-70, or 180 g of hydroxyethyl starch-Hetastarch) is added to 200 ml of an anhydrous organic solvent (e.g., acetone, methylene chloride, dimethylsulfoxide, benzene, or 1,4-dioxane) at room temperature. Separately, N-succinimidyl chloroformate (6 mmol) is dissolved in 10 ml of dry acetone. Separately, 4-(dimethylamino) pyridine is dissolved in 10 ml of dry acetone. The succinimidyl chloroformate solution is added to the sedimentation agent solution with stirring. Next, the 4-(dimethylamino) pyridine solution is added to the combined succinimidyl chloroformate/sedimentation agent reaction solution. The solution is stirred for 2 hours at room temperature. The solution is filtered to remove precipitated 4-(dimethylamino) pyridine hydrochloride byproduct. A non-polar organic solvent (e.g., petroleum ether or diethyl ether) (500 ml) is added to the filtrate to precipitate the succinimidyl carbonate activated sedimentation agent. The activated sedimentation agent is collected by filtration. The activated sedimentation agent precipitate is further cleaned by re-dissolving in the organic solvent, filtering, precipitating in the non-polar solvent, and filtering. The antibody or antibodies (100 mg, 0.67 μmol (ea)) to be linked to the sedimentation agent is dissolved in 20 ml of buffer (e.g., 0.1M sodium phosphate at pH 7.5) at a concentration of 5 mg/ml. The activated sedimentation agent (10 μmol per antibody) (approximately 0.2 g of PEG-20K, 0.7 g of Dextran-70, or 1.8 g of hydroxyethyl starch-Hetastarch) is slowly added to the reaction solution in an ice-bath (temperature of about 4° C.). The solution is stirred for one hour at 4° C. The final ALISA is isolated or concentrated (e.g., via dialysis membranes, affinity column chromatography, or gel filtration).

Example 3

ALISA Preparation using N,N'-Carbonyldiimidazole

In this Example, ALISA is prepared using N,N'-carbonyldiimidazole (CDI). The sedimentation agent (1 mmol) (approximately 20 g of polyethylene glycol-PEG-20,000, 70 g of dextran-Dextran-70, or 180 g of hydroxyethyl starch-Hetastarch) is added to 200 ml of an anhydrous organic solvent (e.g., acetone, methylene chloride, dimethylsulfoxide, benzene, or 1,4-dioxane) at room temperature. Separately, CDI (6 mmol) is dissolved in 10 ml of the organic solvent. The CDI solution is added to the sedimentation agent solution with stirring. The combined reaction solution is stirred for 2 hours at 37° C. The reaction solution is then added to a non-polar organic solvent (e.g., petroleum ether or diethyl ether) (500 ml) to precipitate the CDI activated sedimentation agent. The activated sedimentation agent is collected by filtration. The activated sedimentation agent precipitate is further cleaned by re-dissolving in the organic solvent, filtering, precipitating in the non-polar solvent, and filtering. The antibody or antibodies (100 mg, 0.67 μmol (ea)) to be linked to the sedimentation agent is dissolved in 20 ml of buffer (e.g., 0.1 M sodium carbonate at pH 9-10) at a concentration of 5 mg/ml. The activated sedimentation agent 10 μmol per antibody (approximately 0.2 g of PEG-20K, 0.7 g of Dextran-70, or 1.8 g of hydroxyethyl starch-Hetastarch) is slowly added to the reaction solution in an ice-bath (temperature of about 4° C.). The solution is stirred for 48 hours at 4° C. The final ALISA is isolated or concentrated (e.g., via dialysis membranes, affinity column chromatography, or gel filtration).

Example 4

ALISA Preparation using a Moffatt Oxidation followed by Reductive Amination

In this Example, ALISA is prepared using a Moffatt oxidation followed by reductive amination. The sedimentation agent 1 mmol (approximately 20 g of polyethylene glycol-PEG-20,000, 70 g of dextran-Dextran-70, or 180 g of hydroxyethyl starch-Hetastarch) is added to 100-200 ml of an anhydrous dimethylsulfoxide at room temperature. The solution may be heated to dissolve the sedimentation agents, but should be cooled back to room temperature once dissolved. Separately, acetic anhydride (3 ml, 30 mmol) is added dropwise to the solution, followed by the addition of 5 ml of triethylamine. The combined reaction solution is stirred for 24 hours at room temperature. The reaction solution is then added to a non-polar organic solvent (e.g., petroleum ether or diethyl ether) (500 ml) to precipitate the aldehyde activated sedimentation agent. The activated sedimentation agent is collected by filtration. This activated sedimentation agent precipitate is further cleaned by re-dissolving in the organic solvent, filtering, precipitating in the non-polar solvent, and filtering. The antibody or antibodies (100 mg, 0.67 μmol (ea)) to be linked to the sedimentation agent is dissolved in 20 ml of buffer (e.g., 0.1M 4-(2-hydroxyethyl)-1-piperazineethanesulfonic acid (HEPES) at pH 7.5) at a concentration of 5 mg/ml. Separately, sodium cyanoborohydride (10 mM, 0.628 mg) is added to the reaction solution. The activated sedimentation agent (10 μmol per antibody) (approximately 0.2 g of PEG-20K, 0.7 g of Dextran-70, or 1.8 g of hydroxyethyl starch-Hetastarch) is slowly added to the reaction solution at 4° C. The reaction solution is stirred for 24 hours at 4° C. The reaction is quenched by the addition of ethanolamine (10 mM, 0.611 mg) and stirring for 2 hours. The final ALISA is isolated or concentrated (e.g., via dialysis membranes, affinity column chromatography, or gel filtration).

Example 5

(Strept)avidin-Sedimentation Agent Preparation using Tricholor-s-triazine

In this Example, a (strept)avidin-sedimentation agent is prepared using Tricholor-s-triazine. Anhydrous sodium carbonate (1 g) is added to 200 ml of anhydrous organic solvent (e.g., acetone, methylene chloride, dimethylsulfoxide, benzene, or 1,4-dioxane). 0.55 g of trichloro-s-triazine (TsT) is then dissolved in the reaction solution. The sedimentation agent (1 mmol) (approximately 20 g of polyethylene glycol-PEG-20,000, 70 g of dextran-Dextran-70, or 180 g of hydroxyethyl starch-Hetastarch) is added to the reaction solution. The reaction solution is then stirred overnight at room temperature. The reaction solution is then filtered. The filtrate is then added to a sufficient amount of a non-polar organic solvent (e.g., petroleum ether or diethyl ether) (500 ml) to produce a precipitate that is collected by filtration.

This activated sedimentation agent precipitate is further cleaned by re-dissolving in the organic solvent, filtering, precipitating in the nonpolar solvent, and filtering. (Strep) avidin (100 mg) to be linked to the sedimentation agent is dissolved in 20 ml of buffer (e.g., 0.1 M sodium borate at pH 9.4) at a concentration of 5 mg/ml. The activated sedimentation agent (10 µmol) (approximately 0.2 g of PEG-20K, 0.7 g of Dextran-70, or 1.8 g of hydroxyethyl starch-Hetastarch) is slowly added to the reaction solution in an ice-bath (temperature 4° C.). The reaction solution is stirred for one hour at 4° C. The final (strept)avidin-sedimentation agent is isolated or concentrated (e.g., via dialysis membranes, affinity column chromatography, or gel filtration).

Example 6

(Strept)avidin Sedimentation Agent Preparation using N-Succinimidyl Chloroformate In this Example, (strept)avidin sedimentation agent is prepared using N-succinimidyl chloroformate. The sedimentation agent (1 mmol) (approximately 20 g of polyethylene glycol-PEG-20,000, 70 g of dextran-Dextran-70, or 180 g of hydroxyethyl starch-Hetastarch) is added to 200 ml of an anhydrous organic solvent (e.g., acetone, methylene chloride, dimethylsulfoxide, benzene, or 1,4-dioxane) at room temperature. Separately, N-succinimidyl chloroformate (6 mmol) is dissolved in 10 ml of dry acetone. Separately, 4-(dimethylamino)pyridine is dissolved in 10 ml of dry acetone. The succinimidyl chloroformate solution is added to the sedimentation agent solution with stirring. Next, 4-(dimethylamino)pyridine solution is added to the combined reaction solution. The combined reaction solution is stirred for 2 hours at room temperature. The reaction solution is filtered to remove the precipitated 4-(dimethylamino) pyridine hydrochloride byproduct. A non-polar organic solvent (e.g., petroleum ether or diethyl ether) (500 ml) is added to the filtrate to precipitate the succinimidyl carbonate activated sedimentation agent. The activated sedimentation agent is collected by filtration. The activated sedimentation agent precipitate is further cleaned by re-dissolving in the organic solvent, filtering, precipitating in the non-polar solvent, and filtering. The (strept)avidin (100 mg) to be linked to the sedimentation agent is dissolved in 20 ml of buffer (e.g., 0.1 M sodium phosphate at pH 7.5) at a concentration of 5 mg/ml. The activated sedimentation agent (10 µmol) (approximately 0.2 g of PEG-20K, 0.7 g of Dextran-70, or 1.8 g of hydroxyethyl starch-Hetastarch) is slowly added to the reaction solution in an ice-bath (temperature 4° C.). The reaction solution is stirred for one hour at 4° C. The final (strept)avidin-sedimentation agent is isolated or concentrated (e.g., via dialysis membranes, affinity column chromatography, or gel filtration).

Example 7

ALISA Preparation using Biotinylated Antibodies and (Strept)avidin-Sedimentation Agent In this Example, ALISA is prepared using a (strept) avidin-sedimentation agent linked to a biotinylated antibody. The (strept)avidin-sedimentation-linked sedimentation agent synthesized according to Examples 5 or 6 is dissolved in phosphate-buffered saline (PBS) (pH 7.4; osmolarity of 280-300 mosM). The concentration of the (strept)avidin-sedimentation agent is in excess (1.5-10 fold) of the antibody used in the ALISA. The selected biotinylated antibody or antibodies are added to the ALISA solution to achieve a final concentration of about 0.125 µg/ml to about 20 µg/ml per antibody. This antibody concentration is optimized via titration experiments to allow for the minimal use of expensive antibody reagents. The (strept)avidin-sedimentation agent and biotinylated antibody or antibodies are incubated at 0° C.-37° C. for 10-60 minutes. Excess biotin may be further added and incubated to block unoccupied, remaining sites on the (strept)avidin-sedimentation agent. The final (strept)avidin-ALISA is isolated or concentrated (e.g., via dialysis membranes, affinity column chromatography, or gel filtration).

Example 8

Isolation of Lymphocytes by Positive Selection

In this Example, lymphocytes are isolated from whole blood according to the method in a positive selection method. Whole blood (10 ml) is drawn from a patient and collected in a lavender top VACUTAINER collection tube ($K_2$EDTA 1.8 mg/ml blood). Other anticoagulants may work equally, such as 3.2% sodium citrate or 15 USP sodium heparin/ml blood. Other collection systems can also be used including direct syringe draw and blood bag collection systems. ALISA is separately prepared by attaching an anti-CD3 (clone UCHT-1) linked to PEG 20K and anti-CD19 (clone AE1) linked to PEG 20K, as described in Examples 1-4, above. The ALISA solution is added to achieve a final antibody concentration of about 0.125 µg/ml to about 20 µg/ml. The antibody concentration is optimized via titration experiments. In this Example, ALISA 50 µg of each anti-CD3 and anti-CD19 reagent (20 µl each of stock solutions of 1 mg antibody/ml) is added to the whole blood sample. Additionally, 60 µl of unlabeled sedimentation agent (PEG 20K in this Example) is added to achieve a total sedimentation agent concentration of 0.6%. The mixture is vortexed for 30 seconds. The sample is then incubated for 20 minutes at room temperature and is then centrifuged at 1000×g for 10 minutes at room temperature. The unwanted components (platelets, plasma, and neutrophils) remain in the buffy-coat/WBC layer and plasma layer, while the targeted lymphocytes are sedimented within the ALISA-rouleaux/rouleaux networks RBC layer. The unwanted, upper layers are removed, the RBCs are lysed (e.g., ammonium chloride lysis buffer), and the targeted lymphocytes are recovered after washing.

Example 9

Isolation of Pancreatic Islets of Langerhans by Positive Selection

In this Example, cells of pancreatic islets of Langerhans are separated from pancreatic acinar/exocrine and stromal cells in a positive selection method. Pancreas tissue is prepared via the Ricordi method including collagenase treatment and possible trypsin inhibition. In this Example, ALISA 800 µg of anti-insulin antibody (320 µl of stock solutions of 1 mg antibody/ml) is added to 20 ml of the pancreas digestion solution. Anti-glucagon and anti-somatostatin ALISAs may also be used. Unlabeled sedimentation agent (PEG 20K in this Example) (240 µl) is added to achieve a total sedimentation agent concentration of 0.6%.

An additional 20 ml of autologous packed RBCs are added to the mixture. The mixture is vortexed for 30 seconds. The sample is then incubated for 20 minutes at room temperature and is then centrifuged at 1000×g for 10 minutes at room temperature. The unwanted components (acinar/exocrine and stromal cells) remain in the buffy-coat/WBC layer and plasma layer, while the targeted islets are sedimented within the ALISA-rouleaux/rouleaux networks RBC layer. The unwanted, upper layers are removed, the RBCs are lysed (e.g., ammonium chloride lysis buffer), and the targeted islets of Langerhans are recovered after washing.

Example 10

Isolation of CD34+ Stem Cells from Bone Marrow Isolates or Peripheral Blood Stem Cell Isolates by Positive Selection In this Example, CD34+ stem cells are isolated from bone marrow isolates or peripheral blood stem cell isolates in a positive selection method. ALISA is added to the bone marrow or peripheral blood stem cell isolate adjusted to a 100 ml starting volume with PBS. In this Example, ALISA 4 mg of anti-CD34 antibody (4 ml of stock solutions of 1 mg antibody/ml) and an additional 100 ml of autologous packed RBCs are added to the stem cell isolate solution. Unlabeled sedimentation agent (PEG 20K in this Example) (1.2 ml) is added to achieve a total sedimentation agent concentration of 0.6%. The mixture is vortexed for 2 minutes. The sample is then incubated for 30 minutes at room temperature and is then centrifuged at 1000×g for 15 minutes at room temperature. The unwanted components remain in the buffy-coat/WBC layer and plasma/PBS layer, while the targeted CD34+ stem cells are sedimented within the ALISA-rouleaux/rouleaux networks RBC layer. The unwanted, upper layers are removed, the RBCs are lysed (e.g., ammonium chloride lysis buffer), and the targeted CD34+ stem cells are recovered after washing to remove free hemoglobin.

Example 11

Isolation of CD8+ T cells by Negative Selection

In this Example, Cytotoxic CD8+ T cells are isolated from whole blood according to the method in a negative selection method. Whole blood (10 ml) is drawn from a patient and collected in a lavender top VACUTAINER collection tube ($K_2$EDTA 1.8 mg/ml blood). Other anticoagulants may work equally, such as 3.2% sodium citrate or 15 USP sodium heparin/ml blood. Other collection systems can also be used including direct syringe draw and blood bag collection systems. ALISA is separately prepared by attaching an anti-CD4, anti-CD14, anti-CD16, anti-CD19, anti-CD20, anti-CD36, anti-CD56, anti-CD123, anti-TCRγ/δ, and anti-glycophorin A to PEG 20K, as described in Examples 1-4, above. The ALISA solution is added to achieve a final antibody concentration of about 0.125 µg/ml to 20 µg/ml per each antibody. This antibody concentration is optimized via titration experiments. In this Example, ALISA 2.5 µg to 50 µg of each reagent antibody (40 µl each of a combined 9-antibody stock solution 0.1-1 mg/ml of each antibody) is added to the whole blood sample. Additionally, 60 µl of unlabeled sedimentation agent (PEG 20K in this Example) is added to achieve a total sedimentation agent concentration of 0.6%. The mixture is vortexed for 30 seconds. The sample is then incubated for 20 minutes at room temperature and is then centrifuged at 1000×g for 10 minutes at room temperature. The targeted and wanted CD8+ Cytotoxic T cells remain in the buffy-coat/WBC layer, while the unwanted cells (targeted by CD4, CD14, CD16, CD19, CD20, CD36, CD56, CD123, TCRγ/δ, glycophorin A surface markers) are sedimented within the ALISA-rouleaux/rouleaux networks RBC layer.

Example 12

Isolation of HIV-1 Virions by Positive Selection

In this Example, HIV-1 virions are isolated from a sample by a positive selection method. Whole blood (10 ml) is drawn from an HIV-infected patient and collected in a lavender top VACUTAINER collection tube ($K_2$EDTA 1.8 mg/ml blood). The ALISA is separately prepared by attaching an anti-GP120 linked to PEG 20K, as described in Examples 1-4, above. The antibody concentration is optimized via titration experiments. In this Example, the ALISA 50 µg of the antibody (20 µl of stock solutions of 1 mg antibody/ml) is added to the whole blood sample. Additionally, 60 µl of unlabeled sedimentation agent (PEG 20K in this Example) is added to achieve a total sedimentation agent concentration of 0.6%. The mixture is vortexed for 30 seconds. The sample is then incubated for 20 minutes at room temperature and is then centrifuged at 1000×g for 10 minutes at room temperature. The unwanted components (platelets, plasma, and WBCs) remain in the buffy-coat/WBC layer and plasma layer, while the targeted HIV virions are sedimented within the ALISA-rouleaux/rouleaux networks RBC layer. The unwanted, upper layers are removed. The HIV virions and RBCs can be lysed (e.g., ammonium chloride lysis buffer), and the targeted HIV virions can be by quantified by realtime quantitative PCR.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of isolating a target from a sample, the method comprising:
   a) forming a mixture comprising:
      i) a sample, wherein the sample comprises a target and a non-target unwanted component, wherein the non-target unwanted component comprises a non-target antigen;
      ii) red blood cells;
      iii) an antibody-linked immuno-sedimentation agent comprising an antibody directly linked to a soluble sedimentation agent by a non-antigen binding region of the antibody, wherein the antibody is a monoclonal antibody or antigen-binding fragment thereof, and wherein the antibody specifically binds to the non-target antigen; and
      iv) the soluble sedimentation agent, wherein the soluble sedimentation agent is unlabeled and selected from the group consisting of polyethylene glycol, dextran, and hydroxyethyl starch;

b) incubating the mixture of a) under conditions sufficient to form a red blood cell rouleaux complex, comprising the red blood cells, the antibody-linked immuno-sedimentation agent bound to the to the non-target unwanted component, and the unlabeled sedimentation agent;
c) separating the red blood cell rouleaux complex of b) from the mixture by centrifugation and/or sedimentation to form a red blood cell rouleaux layer comprising the non-target unwanted component;
d) removing the red blood cell rouleaux layer of c), thereby removing the non-target unwanted component from the mixture; and
e) recovering the target from the mixture following step d), thereby isolating the target from the sample,
wherein the sedimentation agent of iii) and iv) is present in the mixture of a) in a concentration suitable to induce the formation of the rouleaux in step (b) and to co-sediment the unwanted component into the rouleaux layer in step (c).

2. The method of claim 1, wherein the sample is selected from the group consisting of whole blood, blood plasma, blood stem cell isolates, platelet-rich plasma, fractionated blood, packed red blood cells, umbilical cord blood, bone marrow, bone-marrow aspirates, a buffy-coat layer, a leukapheresis isolate, a plasmapheresis isolate, a cell suspension, a cell culture medium, a cell mixture, a cell homogenate, a pancreas isolate, an organ homogenate, a saline solution, a Ringer's solution, a lactated Ringer's solution, a phosphate buffered saline solution, a viral culture medium, an oocyte mixture, a sperm, a gamete mixture, and combinations thereof.

3. The method of claim 1, wherein the target is selected from the group consisting of: a multicellular organism, a single-cell organism, a cell, a subcellular component, a cellular fragment, a virus, a viroid, a virus-like target, a membrane-bound particle, a lipid particle, a macromolecule, a DNA, a RNA, a nucleic acid-like macromolecule, a peptide, a polypeptide, and a protein.

4. The method of claim 1, wherein recovering the target according to step e) comprises performing at least one of sedimentation, centrifugation, density gradient centrifugation, a magnetic field, an electrical field, cell lysis, chemical crosslinking, extraction, a phase transition, freeze-thaw cycling, evaporation, boiling, subliming, melting, crystallizing, plasticizing, filtration, and combinations thereof.

5. The method of claim 1, further comprising adding a blocking agent to the mixture.

6. The method of claim 1, wherein the antibody is selected from the group consisting of an anti-CD3 antibody, an anti-CD19 antibody, an anti-insulin antibody, an anti-CD34 antibody, an anti-CD4 antibody, an anti-CD14 antibody, an anti-CD16 antibody, an anti-CD19 antibody, an anti-CD20 antibody, an anti-CD36 antibody, an anti-CD56 antibody, an anti-CD123 antibody, an anti-TCRγ/δ antibody, an anti-glycophorin A antibody, and an anti-GP120 antibody.

7. The method of claim 1, wherein the antibody is the monoclonal antibody that specifically binds to the antigen.

8. The method of claim 1, wherein the antibody is the antibody fragment that specifically binds to the antigen.

* * * * *

UNITED STATES PATENT AND TRADEMARK OFFICE
CERTIFICATE OF CORRECTION

PATENT NO. : 11,782,054 B2
APPLICATION NO. : 16/052454
DATED : October 10, 2023
INVENTOR(S) : Warren L. Dinges It is certified that error appears in the above-identified patent and that said Letters Patent is hereby corrected as shown below:

On the Title Page

Item (54), and in the Specification Column 1, Lines 1-4:
"ANTIBODY-LINKED IMMUNO-SEDIMENTATION AGENT AND METHOD OF ISOLATING A TARGET FORM A SAMPLE USING SAME"

Should read:
--ANTIBODY-LINKED IMMUNO-SEDIMENTATION AGENT AND METHOD OF ISOLATING A TARGET FROM A SAMPLE USING SAME--

Signed and Sealed this
Twenty-seventh Day of February, 2024

Katherine Kelly Vidal
*Director of the United States Patent and Trademark Office*